(12) United States Patent
Elworthy

(10) Patent No.: US 7,271,183 B2
(45) Date of Patent: Sep. 18, 2007

(54) 2-PIPERIDONE DERIVATIVES AS PROSTAGLANDIN AGONISTS

(75) Inventor: Todd Richard Elworthy, Los Gatos, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 253 days.

(21) Appl. No.: 10/754,117

(22) Filed: Jan. 8, 2004

(65) Prior Publication Data

US 2004/0142969 A1 Jul. 22, 2004

Related U.S. Application Data

(60) Provisional application No. 60/439,152, filed on Jan. 10, 2003.

(51) Int. Cl.
C07D 211/40 (2006.01)
A61K 31/45 (2006.01)

(52) U.S. Cl. ............................. 514/346; 546/216
(58) Field of Classification Search ................ 546/216; 514/346
See application file for complete search history.

(56) References Cited

U.S. PATENT DOCUMENTS

| | | | |
|---|---|---|---|
| 3,975,399 A | 8/1976 | DeFranco et al. | |
| 4,113,873 A | 9/1978 | Himizu et al. | |
| 4,115,401 A | 9/1978 | Nanthavong et al. | |
| 4,177,346 A | 12/1979 | Nelson | |
| 4,320,136 A | 3/1982 | Scribner | |
| 6,034,093 A | 3/2000 | Ewing et al. | |
| 6,376,533 B1 | 4/2002 | Burk et al. | |
| 6,747,037 B1 * | 6/2004 | Old et al. ................ | 514/277 |

FOREIGN PATENT DOCUMENTS

| | | |
|---|---|---|
| AU | 512960 | 11/1980 |
| BE | 841165 | 10/1976 |
| GB | 1553595 | 10/1979 |
| GB | 1569982 | 6/1980 |
| GB | 1583163 | 1/1981 |
| WO | WO-89/09800 A1 | 10/1989 |
| WO | WO-89/11275 A1 | 11/1989 |
| WO | WO-93/03825 A1 | 3/1993 |
| WO | WO-96/41639 A1 | 12/1996 |
| WO | WO-00/21532 A1 | 4/2000 |
| WO | WO-00/21542 A1 | 4/2000 |
| WO | WO-01/46140 A1 | 6/2001 |
| WO | WO 03/007941 | 1/2003 |
| WO | 2004/085430 * | 10/2004 |

OTHER PUBLICATIONS

Zoretic et al., "Synthesis of (E)-7-[[2-[4(m-Trifluoromethylphenoxy)-3α and 3β-Hydroxy-1-butenyl]-5-oxo-1-pyrrolidinyl]]heptanoic Acids", J. Heterocyclic Chem., Mar.-Apr. 1983, pp. 465-466, 20.
Saijo, et al., "Heterocyclic prostaglandins. IV. Synthesis of 8-aza-11-deoxyprostaglandin $E_1$ and its related compounds,"Yakugaku Zashi, 1980, pp. 3890-3895, 100(4), ABSTRACT.
Suda, et al., "Prostaglandin E Receptor Subtypes in Mouse Osteoblastic Cell Line," Endocrinology, 1996, pp. 1698-1705, 137, No. 5.
Suzawa, et al., "The Role of Prostaglandin E Receptor Subtypes (EP1, EP2, EP3, and EP4) in Bone Resorption: An Analysis Using Specific Agonists for the Respective EPs," Endocrinology, 2000, pp. 1554-1559, 141(4).
Ono, et al., Important role of $EP_4$, a subtype of prostaglandin (PG) E receptor, in osteoclast-like cell formation from mouse bone marrow cells induced by $PGE_2$, Journal of Endocrinology, 1998, pp. R1-R5, 158.
Biaggio, F.C., et al, "The Synthesis of a New i-Azaprostanoid[1]", J. Heterocycl. Chem., May-Jun. 1989, pp. 725-728, vol. 26.

* cited by examiner

Primary Examiner—Rita Desai
(74) Attorney, Agent, or Firm—Robert C. Hall

(57) ABSTRACT

The invention provides compounds of the Formula:

wherein m, n, A, X, Y, Z, $R^1$, $R^2$, $R^4$, $R^6$, $R^7$, $R^8$, $R^9$ and $R^{10}$ are as defined herein, and pharmaceutically acceptable salts, solvates, prodrugs, single isomers or racemic or non-racemic mixture of isomers thereof. The invention also provides methods for preparing, compositions comprising, and methods for using compounds of formula I.

31 Claims, No Drawings

2-PIPERIDONE DERIVATIVES AS PROSTAGLANDIN AGONISTS

CROSS REFERENCE

This application claims the benefit of priority of U.S. Provisional Patent Application Ser. No. 60/439,152, filed Jan. 10, 2003, which is incorporated herein by reference in its entirety.

FIELD OF THE INVENTION

This invention relates to certain 2-pyrrolidone derivatives, and associated pharmaceutical compositions, methods for use as selective prostaglandin $EP_4$ agonists, and methods of preparation thereof.

BACKGROUND OF THE INVENTION

There are many references in the literature to prostaglandins or prostanoids (PGs), a term which is generic to natural and synthetic prostaglandins and prostaglandin-like compounds, and it is well known that even slight differences in their chemical structures or stereochemical configurations will have profound effects on their biological activity.

Prostaglandins or prostanoids (PGs) are a group of bioactive compounds derived from membrane phospholipids, and are formed from 20-carbon essential fatty acids and contain a cyclopentane ring. They fall into several main classes designated by letters and are distinguished by substitutions to the cyclopentane ring. The main classes are further subdivided by subscripts 1, 2, or 3 which reflect their fatty acid precursors.

An example of a particular species of the prostaglandin E is $PGE_2$, with the following structure:

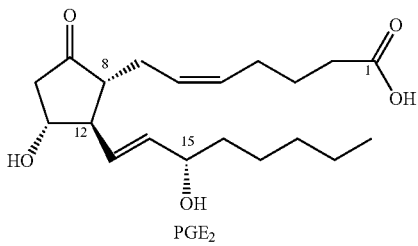

PGE₂

At present four different receptor subtypes of $PGE_2$ are known and they are designated $EP_1$, $EP_2$, $EP_3$, and $EP_4$.

Uses for compounds possessing a strong binding activity to $PGE_2$ receptors comprise the prevention and/or treatment of immunological diseases (autoimmune diseases, organ transplantation, etc.), asthma, abnormal bone formation, neuronal cell death, thrombosis and stroke, hepatopathy, abortion, male and female sexual dysfunction, premature birth, inflammation such as rheumatoid arthritis, retina neuropathy disorders such as glaucoma, hypertension, female fertility disorder, blood clotting disorder, renal disfunction, dry eye, ichthyosis, elevated intraocular pressure, sleep disorders, gastric ulcer, preterm labor, dysmenorrhea, destructive bone loss, preeclampsia, eclampsia, or eosinophil disorder.

Prostaglandins and their associated receptors are more fully described in for example: M. Abramovitz et al., The Utilization of Recombinant Prostanoid Receptors to Determine the Affinities and Selectivities of Prostaglandins and Related Analogs, Biochimica et Biophysica Acta 2000, 1483, 285-293.

The involvement of prostaglandin E receptor agonists in bone resorption is described in, e.g., T. Suzawa et al., The Role of Prostaglandin E Receptor Subtypes in Bone Resorption: An Analysis Using Specific Agonists for the Respective EPs, Endocrinology 2000, 141, 1554-1559; K. Ono et al., Important Role of $EP_4$, a Subtype of Prostaglandin (PG) E Receptor, in Osteoclast-like Cell Formation from Mouse Bone Marrow Cells Induced by $PGE_2$, J. of Endocrinology 1998, 158, R1-R5; M. Suda et al., Prostaglandin E Receptor Subtypes in Mouse Osteoblastic Cell Line, Endocrinology 1996, 137, 1698-1705.

These selective prostaglandin E receptor agonists are also useful for the treatment of gastric lesions, see e.g. H. Araki, et al. The Roles of Prostaglandin E Receptor Subtypes in the Cytoprotective Action of Prostaglandin $E_2$ in Rat Stomach, Aliment. Pharmacol. Ther. 2000, 14 (Suppl. 1), 116-124; T. Kunikata, et al, E Type Prostaglandin Inhibits Indomethacin-Induced Small Intestinal Lesions Through $EP_3$ and $EP_4$ Receptors: A Study Using Rats and Knockout Mice, Gastroenterology 118, abstract #3787.

Other uses of prostaglandin E receptor agonists are for improvement of kidney function as described in, e.g., M. D. Breyer, et al, Prostaglandin E Receptors and the Kidney, Am. J. Physiol. 2000, 279, F12-F23, and K. E. Purdy, et al., $EP_1$ and $EP_4$ Receptors Mediate Prostaglandin $E_2$ Actions in the Microcirculation of Rat Kidney, Am. J. Physiol. 2000, 279, F755-F764; for thrombosis and stroke as well as for other conditions where an inhibition of platelet aggregation would be beneficial as described in, e.g., B. Z. S. Paul, et al, Distribution of Prostaglandin IP and EP Receptor Subtypes and Isoforms in Platelets and Human Umbilical Artery Smooth Muscle Cells, Br. J. Haematol. 1998, 102, 1204-1211; for antiinflammatory effects through inhibition of TNF-alpha generation as described in, e.g. K. K. Meja, et al. Characterization of prostanoid receptor(s) on human blood monocytes at which prostaglandin E2 inhibits lipopolysaccharide-induced tumor necrosis factor-alpha generation, Br. J. Pharmacol. 1997, 122, 149-157, and A. Eigler, et al. Anti-inflammatory activities of cAMP-elevating agents: enhancement of IL-10 synthesis and concurrent suppression of TNF production, J. Leukoc. Biol. 1998, 63, 101-107; or for glaucoma as described in, e.g., M. Takamatsu, et al. Localization of Prostaglandin E Receptor Subtypes in The Ciliary Body of Mouse Eye, Exp. Eye Res. 2000, 70, 623-628, and D. F. Woodward, et al, Molecular Characterization and Ocular Hypotensive Properties of the Prostanoid $EP_2$ Receptor, J. Ocul. Pharmacol. Ther. 1995, 11, 447.

Treatment of impotence and/or erectile dysfunction by using prostaglandins that are selective $EP_2$ and/or $EP_4$ receptor ligands have been disclosed in International Application Publication No. WO 99/02164 assigned to Pharmacia & Upjohn AB.

Additional information relating to prostaglandins and their receptors is described in Goodman & Gillman's, The Pharmacological Basis of Therapeutics, ninth edition, McGraw-Hill, New York, 1996, Chapter 26, pages 601-616.

8-Aza-11-deoxy-prostaglandin analogs corresponding to $PGE_2$ would have the following structure:

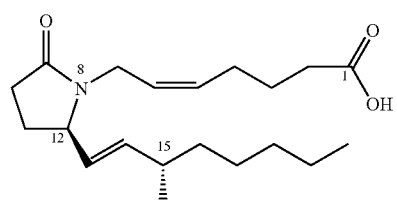

8-Aza-11-deoxy-prostaglandin

Substitution of a nitrogen for the carbon at C-8 causes a change in the three dimensional conformation of the resultant prostaglandin, and because structure is related to biological activity, such a conformational change will have a significant effect upon the biological activity. 8-Aza-11-deoxy prostaglandin E's with the natural side chains have been reported in the literature, see e.g. BE 841,165, assigned to Syntex USA, Inc.

SUMMARY OF THE INVENTION

This invention relates to compounds represented by Formula I:

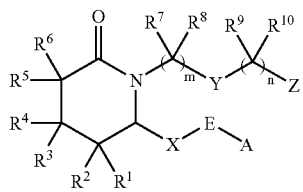

I wherein:

m is from 1 to 4;

n is from 0 to 4;

A is alkyl, aryl, heteroaryl, arylalkyl, arylcycloalkyl, cycloalkylalkyl, or aryloxyalkyl;

E is —CHOH— or —C(O)—;

X is —(CH$_2$)$_2$— or —CH=CH—;

Y is, —CH$_2$—, arylene, heteroarylene, —CH=CH—, —O—, —S(O)$_p$— where p is from 0 to 2, or —NR$^a$—where R$^a$ is hydrogen or alkyl;

Z is —CH$_2$OH, —CHO, tetrazol-5-yl, or —COOR$^b$ where R$^b$ is hydrogen or alkyl; and R$^1$, R$^2$, R$^3$, R$^4$, R$^5$, R$^6$, R$^7$, R$^8$, R$^9$ and R$^{10}$ each independently are hydrogen or alkyl;

or a pharmaceutically acceptable salt or solvate, prodrug, single isomer or racemic or non-racemic mixture of isomers thereof.

The subject compounds have high selectivity in their EP$_4$ receptor agonist activity. The increase in selectivity would alleviate the severe side effects frequently observed following administration of non-selective prostaglandin agonists. Therefore compounds of this invention are desirable.

In another aspect the invention relates to pharmaceutical compositions containing a therapeutically effective amount of at least one compound of Formula I or its pharmaceutically acceptable salt or solvate, prodrug, single isomer or racemic or non-racemic mixture of isomers in admixture with at least one suitable carrier, diluent or excipient.

In another aspect the invention provides a method of treatment of a disease, in particular a bone disease, in a mammal treatable by administration of a prostaglandin EP$_4$ receptor agonist, comprising administration of a therapeutically effective amount of a compound of Formula I or its pharmaceutically acceptable salt.

In another aspect the invention provides a process for preparing compounds of Formula I.

DEFINITIONS

Unless otherwise stated, the following terms used in the specification and claims have the meanings given below:

"Alkoxy" means a radical —OR where R is an alkyl as defined herein e.g., methoxy, ethoxy, propoxy, butoxy and the like.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkylthio" means a radical —SR where R is an alkyl as defined above e.g., methylthio, ethylthio, propylthio, butylthio, and the like.

"Aryl" means a monovalent monocyclic or bicyclic aromatic hydrocarbon radical which is optionally substituted independently from each other with one or more substituents, preferably one, two, or three, selected from the group consisting of alkyl, haloalkyl, halo, nitro, cyano, amino, methylenedioxy, ethylenedioxy, optionally substituted phenyl, aryl, arylalkyl, heteroaryl, heteroarylalkyl, cycloalkyl, cycloalkylalkyl, heterocyclyl, heteroclylalkyl —V—OR', —V—NR'R", —V—C(O)—R', —V—S(O)$_{0-2}$—R'; —V—N—SO$_2$—R', —V—SO$_2$—NR'R", —V—N—C(O)—NR'R", where V is a bond or a C$_1$-C$_3$ alkylene group, and R' and R" are each independently from each other hydrogen, alkyl, haloalkyl, hydroxy, alkoxy, optionally substituted phenyl, heteroaryl, cycloalkyl, or heterocyclyl. More specifically the term aryl includes, but is not limited to, phenyl, chlorophenyl, methoxyphenyl, methoxymethylphenyl, phenyloxyphenyl, 1-naphthyl, 2-naphthyl, and the derivatives thereof. "Arylene" means a divalent monocyclic or bicyclic aromatic hydrocarbon radical and includes divalent versions of the aryl radicals described above.

"Arylalkyl" and "Aralkyl", which may be used interchangeably, mean a radical —R$^a$R$^b$ where R$^a$ is an alkylene group and R$^b$ is an aryl group as defined herein; e.g., benzyl, phenylethyl, 3-(3-chlorophenyl)-2-methylpentyl, and the like are examples of arylalkyl.

"Arylcylcoalkyl" means a radical —R$^a$R$^b$ wherein R$^a$ is cycloalkylene as defined herein and R$^b$ is aryl as defined herein.

"Aryloxy" means a radical —OR$^a$ wherein R$^a$ is aryl as defined herein.

"Aryloxyalkyl means a radical —R$^a$R$^b$ wherein —R$^a$ is alkylene as defined herein and R$^b$ is aryloxy as defined herein.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof. "Cycloalkylene" means a divalent saturated carbocyclic moiety consisting of mono- or bicyclic rings, including divalent versions of the cycloalkyls noted above.

"Cycloalkylalkyl" means a moiety of the formula —R'—R", where R' is alkylene and R" is cycloalkyl as defined herein.

"Halo" means fluoro, chloro, bromo, or iodo, preferably fluoro and chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently from each other with one or more substituents, preferably one or two substituents, selected from alkyl, haloalkyl, halo, nitro, cyano, amino, methylenedioxy, optionally substituted phenyl, aryl, arylalkyl, cycloalkyl, cycloalkylalkyl, heterocyclyl, heterocyclylalkyl, —V—OR', —VNR'R", —V—C(O)—R', —V—O—C(O)—R', —V—S(O)$_{0-2}$—R'; —V—N—SO$_2$—R', —V—SO$_2$—NR'R", —V—N—C(O)—N—R'R", where V is absent or is a $C_1$-$C_3$ alkylene group and R' and R" are each independently from each other hydrogen, alkyl, haloalkyl, hydroxy, alkoxy, optionally substituted phenyl, cycloalkyl, heterocyclyl. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof. "Heteroarylene" means a divalent monocyclic or bicyclic radical of 5 to 12 ring atoms having at least one aromatic ring containing one, two, or three ring heteroatoms selected from N, O, or S, the remaining ring atoms being C, with the understanding that the attachment points of the heteroarylene radical will be on an aromatic ring. "Heteroarylene includes divalent versions of the heteroaryl radicals described above.

"Heteroarylalkyl" means a moiety of the formula —R'—R", where R' is alkylene and R" is heteroaryl as defined herein.

"Heterocyclyl" means a saturated or unsaturated non-aromatic cyclic radical of 3 to 8 ring atoms in which one or two ring atoms are heteroatoms selected from N, O, or $S(O)_{0-2}$, the remaining ring atoms being C, where one or two C atoms may optionally be replaced by a carbonyl group. The heterocyclyl ring may be optionally substituted independently from each other with one, two, or three substituents selected from alkyl, haloalkyl, halo, nitro, cyano, —V-optionally substituted phenyl, aryl, arylalkyl, heteroaryl, heteroarylalkyl, cycloalkyl, cycloalkylalkyl, —V—OR', —VNR'R", —V—C(O)—R', —V—S(O)$_{0-2}$—R'; —V—NR'—SO$_2$—R", —V—SO$_2$—NR'R", —V—N—C(O)—N—R'R", where V is absent or is a $C_1$-$C_3$ alkylene group and R' and R" are each independently from each other hydrogen, alkyl, haloalkyl, hydroxy, alkoxy, optionally substituted phenyl, heteroaryl or cycloalkyl. More specifically the term heterocyclyl includes, but is not limited to, tetrahydropyranyl, piperidinyl, N-methylpiperidin-3-yl, piperazinyl, N-methylpyrrolidin-3-yl, 3-pyrrolidinyl, morpholinyl, thiomorpholinyl, thiomorpholino-1-oxide, thiomorpholino-1,1-dioxide, pyrrolinyl, imidazolinyl, N-methanesulfonyl-piperidin-4-yl, and the derivatives thereof.

"Heterocycloalkyl" means a moiety of the formula —R'—R", where R' is alkylene and R" is heterocyclyl as defined herein.

"Leaving group" has the meaning conventionally associated with it in synthetic organic chemistry, i.e., an atom or a group capable of being displaced by a nucleophile and includes halo (such as chloro, bromo, and iodo), alkylsulfonyloxy, arylsulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optionally substituted phenyl" means a phenyl ring which is optionally substituted independently from each other with one or more substituents, preferably one or two substituents selected from the group consisting of alkyl, hydroxy, alkoxy, haloalkyl, haloalkoxy, heteroalkyl, halo, nitro, cyano, amino, methylenedioxy, ethylenedioxy and acyl.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, *Angew. Chem. Inter. Edit*. 1966, 5, 385; errata 511; Cahn et al., *Angew. Chem*. 1966, 78, 413; Cahn and Ingold, *J. Chem. Soc*. 1951 (London), 612; Cahn et al., *Experientia* 1956, 12, 81; Cahn, J., *Chem. Educ*. 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

"Atropic isomers" means the isomers owing their existence to restricted rotation caused by hindrance of rotation of large groups about a central bond.

The compounds of this invention may exist in stereoisomeric form, therefore they can be produced as individual stereoisomers or as mixtures.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same acid addition salt. "Crystal forms" (or polymorphs) means crystal structures in which a compound can crystallize in different crystal packing arrangements, all of which have the same elemental composition. Different crystal forms usually have different X-ray diffraction patterns, infrared spectra, melting points, density hardness, crystal shape, optical and electrical properties, stability and solubility. Recrystallization solvent, rate of crystallization, storage temperature, and other factors may cause one crystal form to dominate.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, or sulfhydryl group, respectively. Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p1-92, Elesevier, New York-Oxford (1985).

"Protecting group" (PG) refers to a grouping of atoms that when attached to a reactive group in a molecule masks, reduces or prevents that reactivity. Examples of protecting groups can be found in T. W. Green and P. G. M. Futs, *Protective Groups in Organic Chemistry*, (Wiley, 3$^{rd}$ ed. 1999) and Harrison and Harrison et al., *Compendium of Synthetic Organic Methods*, Vols. 1-8 (John Wiley and Sons, 1971-1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Prostaglandin analog" is a non-naturally-occurring compound which is structurally similar to a prostaglandin.

"Prostaglandin receptor" or "prostanoid receptor' is a naturally-occurring protein that binds prostaglandins, which when bound alters the function of a cell. Prostaglandin receptors may be characterized as either excitatory or relaxant. Such receptors include but are not limited to $EP_1$, $EP_2$, $EP_3$, $EP_4$, DP, FP, IP, $TP_1$, and $TP_2$. These receptors are further discussed by Coleman et al, in *Pharmacological Reviews*, 1994, Volume 6, No. 2, pages 205-229.

Nomenclature and Structures

In general, the nomenclature used in this Application is based on AUTONOM™ v.4.0, a Beilstein Institute computerized system for the generation of IUPAC systematic nomenclature. Chemical structures shown herein are prepared using ISIS® v. 4.0. Any open valency appearing on a carbon, oxygen or nitrogen atom in the structures herein indicates the presence of a hydrogen.

Compounds

The invention provides compounds of Formula I:

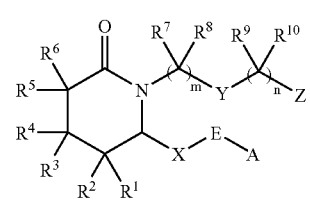

wherein:

m is from 1 to 4; preferably m is 2;

n is a bond or from 1 to 4; preferably n is 3;

A is alkyl, aryl, heteroaryl, arylalkyl, arylcycloalkyl, cycloalkylalkyl, or aryloxyalkyl;

E is —CHOH— or —C(O)— (i.e., E is hydroxymethylene or oxo); preferably E is —CHOH— (hydroxymethylene);

X is —(CH$_2$)$_2$— or —CH=CH—;

Y is —CH$_2$—, arylene, heteroarylene, —CH=CH—, —O—, —S(O)$_p$— where p is from 0 to 2, or —NR$^a$—where R$^a$ is hydrogen or alkyl; preferably Y is —CH$_2$— or —S(O)$_p$—, with p preferably being 0;

Z is —CH$_2$OH, —CHO, tetrazol-5-yl, or —COOR$^b$ where R$^b$ is hydrogen or alkyl; preferably Z is —COOR$^b$ and R$^b$ is hydrogen;

R$^1$, R$^2$, R$^3$, R$^4$, R$^5$, R$^6$, R$^7$, R$^8$, R$^9$ and R$^{10}$ each independently are hydrogen or alkyl; preferably R$^1$, R$^2$, R$^3$, R$^4$, R$^5$, R$^6$, R$^7$, R$^8$, R$^9$ and R$^{10}$ are hydrogen;

or a pharmaceutically acceptable salt or solvate, prodrug, single isomer or racemic or non-racemic mixture of isomers thereof.

Where any of R$^1$, R$^2$, R$^3$, R$^4$, R$^5$, R$^6$, R$^7$, R$^8$, R$^9$ R$^{10}$, R$^a$ and R$^b$ are alkyl, they preferably are lower alkyl, i.e. C$_{1-6}$alkyl, and more preferably C$_{1-4}$alkyl.

In certain embodiments, m is 2, n is 3, E is —CHOH—, Y is —S— or —CH$_2$—, Z is —COOR$^b$, and R$^1$, R$^2$, R$^3$, R$^4$, R$^5$, R$^6$, R$^7$, R$^8$, R$^9$ and R$^{10}$ are hydrogen. In such embodiments compounds of Formula I may be represented by Formula II:

wherein A, X, and R$^b$ are as defined herein. In preferred embodiments, the stereochemistry may be such that compounds of Formula II are more specifically of Formula III:

In other embodiments, m is 2, n is 0, E is —CHOH—, Y is arylene or phenylene, Z is —COOR$^b$, and R$^1$, R$^2$, R$^3$, R$^4$, R$^5$, R$^6$, R$^7$, R$^8$, R$^9$ and R$^{10}$ are hydrogen. In such embodiments compounds of Formula I may be represented by Formula IV:

The stereochemistry may be such that compounds of Formula IV are more specifically of Formula V:

Representative compounds in accordance with the invention are shown in Table 1.

TABLE 1

| Name (Autonom ®) | Structure | Mass Spec (MW) |
| --- | --- | --- |
| 1  4-{2-[2R-(5-cyclopropyl-3S-hydroxy-pent-1E-enyl)-6-oxo-piperidin-1-yl]ethylsulfanyl}butyric acid | 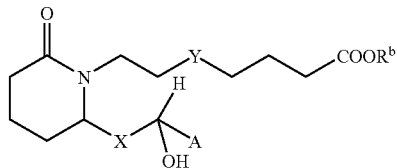 | 369 |

TABLE 1-continued

| | Name (Autonom ®) | Structure | Mass Spec (MW) |
|---|---|---|---|
| 2 | 4-(2-{2R-[3R-(4'chloro-2'methylbiphenyl-3-yl)-3-hydroxy-propyl]-6-oxo-piperidin-1-yl}-ethylsulfanyl)butyric acid | 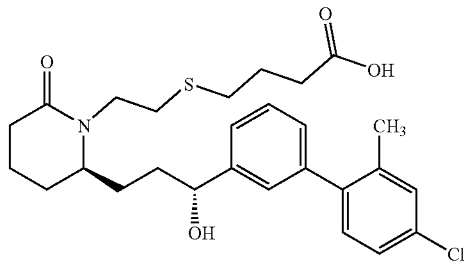 | 503.5 |
| 3 | 7-{2R-[3S-hydroxy-4-(4-hydroxy-3-methyl-phenyl)-but-1E-enyl]-6-oxo-piperidin-1-yl}heptanoic acid | 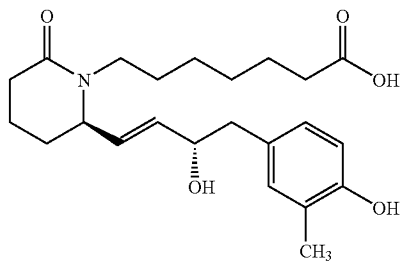 | 403 |
| 4 | 7-{2R-[3S-hydroxy-4-(3-methoxymethyl-phenyl)-but-1E-enyl]-6-oxo-piperidin-1-yl}heptanoic acid | 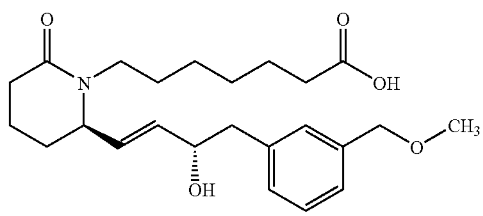 | 417 |
| 5 | 7-{2R-[3S-hydroxy-4-(4-hydroxy-3-isopropyl-phenyl)-but-1E-enyl]-6-oxo-piperidin-1-yl}heptanoic acid | 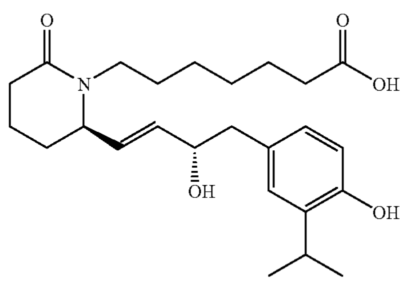 | 431 |
| 6 | 4-(2-{2R-[3-hydroxy-3-(1-phenylcyclopropyl)-prop-1E-enyl]-6-oxo-piperidin-1-yl}ethylsulfanyl)butyric acid | 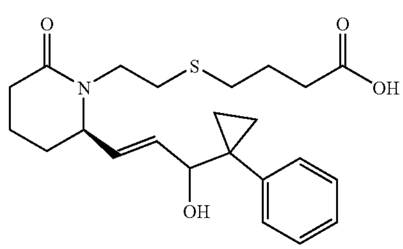 | 417 |
| 7 | 4-(2-{2R-[3R-3-hydroxy-3-(trifluoromethyl-furan-2-yl)-propyl]-6-oxo-piperidin-1-yl}-ethylsulfanyl)butyric acid | 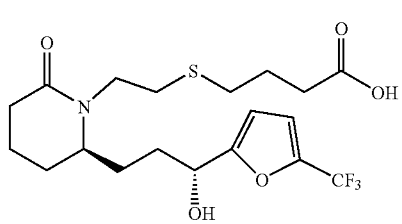 | 437 |

TABLE 1-continued

| Name (Autonom ®) | Structure | Mass Spec (MW) |
| --- | --- | --- |
| 8 4-(2-{2R-[3R-hydroxy-3-(1-phenylcyclopropyl)-propyl]-6-oxo-piperidin-1-yl}ethylsulfanyl) butyric acid | | 419 |
| 9 4-(2-{2R-[3S-hydroxy-4-(3-methoxymethyl-phenyl)-but-1E-enyl]-6-oxo-piperidin-1-yl}ethylsulfanyl) butyric acid | | 435 |
| 10 7-{2R-[3R-(4'hydroxy-2'-methylbiphenyl-3-yl)-3-hydroxy-propyl]-6-oxo-piperidin-1-yl} heptanoic acid | | 467 |
| 11 7-{2R-[3-hydroxy-3-(4'hydroxy-2'methylbiphenyl-3-yl)-prop-1E-enyl]-6-oxo-piperidin-1-yl}heptanoic acid | | 465 |
| 12 7-(2-{2R-[3R-(4'hydroxy-2'methylbiphenyl-3-yl)-3-oxo-propyl]-6-oxo-piperidin-1-yl} heptanoic acid | | 465 |

TABLE 1-continued

| Name (Autonom ®) | Structure | Mass Spec (MW) |
|---|---|---|
| 13 4-{2-[2R-(5-cyclobutyl-3S-hydroxy-pent-1E-enyl)-6-oxo-piperidin-1-yl]ethylsulfanyl}butyric acid | | 383 |
| 14 4-(2-{2R-[3R-(3'-fluorophenoxy-phenyl-3-yl)-3-hydroxy-propyl]-6-oxo-piperidin-1-yl}-ethylsulfanyl)-3-methyl butyric acid | | 503 |
| 15 4-{2-[2R-(3-hydroxy-4,4-dimethyl-oct-1E-enyl)-6-oxo-piperidin-1-yl]-ethylsulfanyl}butyric acid | | 399 |
| 16 7-{2R-[3-hydroxy-3-(2,5-dimethylphenyl-3-yl)-prop-1E-enyl]-6-oxo-piperidin-1-yl}heptanoic acid | | 387 |
| 17 7-[-2R-(3-hydroxy-4-phenoxy-but-1E-enyl)-6-oxo-piperidin-1-yl]heptanoic acid | | 389 |
| 18 7-{2R-[3-hydroxy-3-(3'chloro-biphenyl-3-yl)-prop-1E-enyl]-6-oxo-piperidin-1-yl}heptanoic acid | | 470.5 |

TABLE 1-continued

| | Name (Autonom ®) | Structure | Mass Spec (MW) |
|---|---|---|---|
| 19 | 7-{2R-[3R-(3'chloro-biphenyl-3-yl)-3-hydroxy-propyl[-6-oxo-piperidin-1-yl}heptanoic acid | 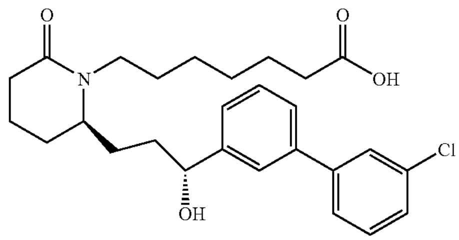 | 472.5 |
| 20 | 4-(2-{2-[3-hydroxy-4-(3-trifluoromethyl-phenyl)-but-1E-enyl]-6-oxo-piperidin-1-yl}-ethyl) benzoic acid | 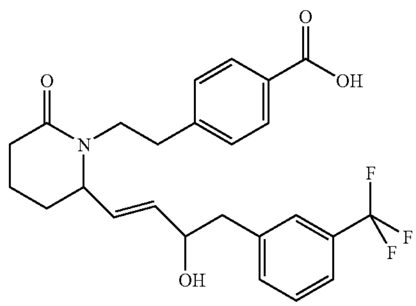 | 461 |
| 21 | 4-(2-{2-[3-hydroxy-3-(4'chloro-2'-methyl-biphen-3-yl)-propyl]-6-oxo-piperidin-1-yl}-ethyl) benzoic acid | 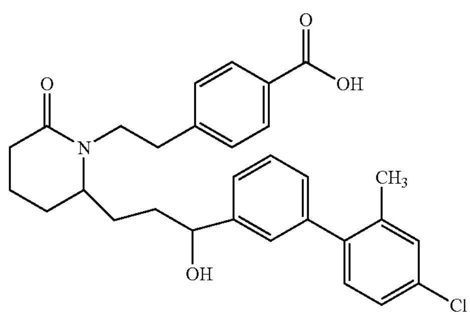 | 506.5 |

The compounds of the invention are capable of further forming pharmaceutically acceptable base addition salts. All of these forms are considered to be within the scope of the present invention.

Synthesis

Compounds of the invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Schemes A, B, and C below illustrate synthetic procedures usable to prepare compounds of Formula I, wherein LG is a leaving group, PG is a protecting group, R is any lower alkyl and may be the same or different in each occurrence, and m, n, A, X, Y, Z, $R^1$, $R^2$, $R^4$, $R^6$, $R^7$, $R^8$, $R^9$ and $R^{10}$ are as defined herein. Specific examples of the procedure of Scheme A are provided in the following Experimental section.

SCHEME A

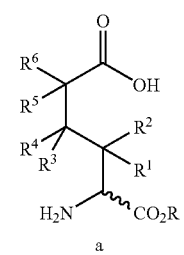

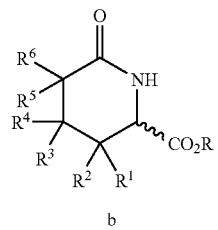

Scheme A illustrates the preparation of In step 1 of Scheme A, an amino adipic acid a is cyclized to form a delta-lactam b. Various amino adipic acids of R and S configuration usable in step 1 are commercially available or may be prepared via well known techniques. The cyclization of this step may be carried out, for example, by simple heating of the amino adipic acid in acetic acid or other polar protic solvent conditions preferably under acidic conditions.

Reduction of a carboxylate group of delta lactam b is carried out in step 2, followed by protection of the reduction product to yield a protected alcohol c. The reduction of step 2 may be achieved by, for example, treatment of delta lactam b with an alkalai metal borohydride or cyanoborohydride under mild, polar protic conditions. The resulting alcohol (not shown) may then be protected, for example, by treatment with alkyl vinyl ether in the presence of trifluoroacetic acid to protect the alcohol as an acetal. The protection of hydroxyl groups via acetal formation is described by S. Saijo et al. *Chem. Pharm. Bull.* 1980, 28, 1449-1458. Protection of the hydroxyl of compound c may also be achieved via silylation as described in T. W. Green and P. G. M. Futs, *Protective Groups in Organic Chemistry*, (Wiley, $3^{rd}$ ed. 1999).

Scheme B below illustrates the preparation of compounds of Formula I. The procedure of Scheme B may be used in embodiments wherein Y is O, S or $NR^a$ or wherein Y can otherwise act as a nucleophile.

SCHEME B

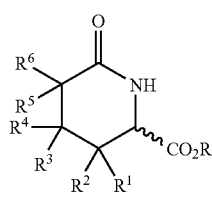

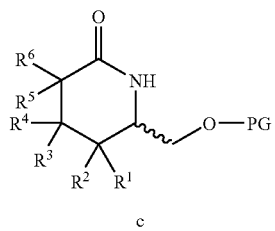

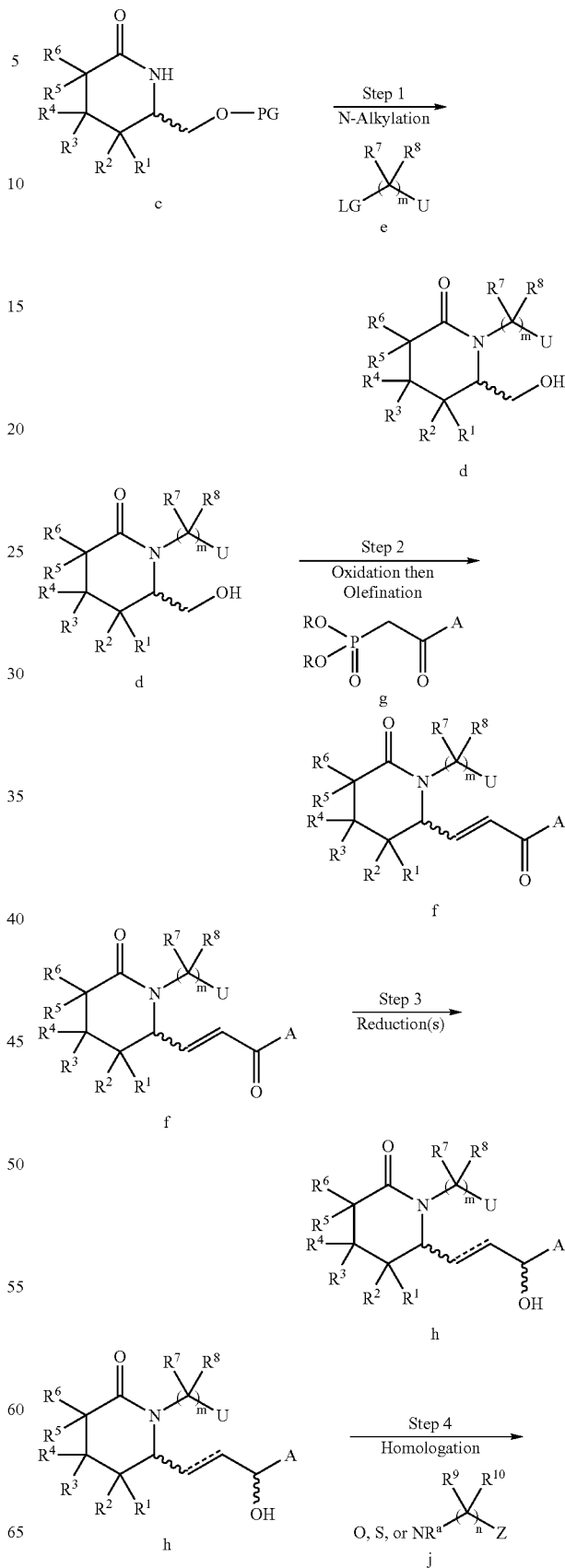

-continued

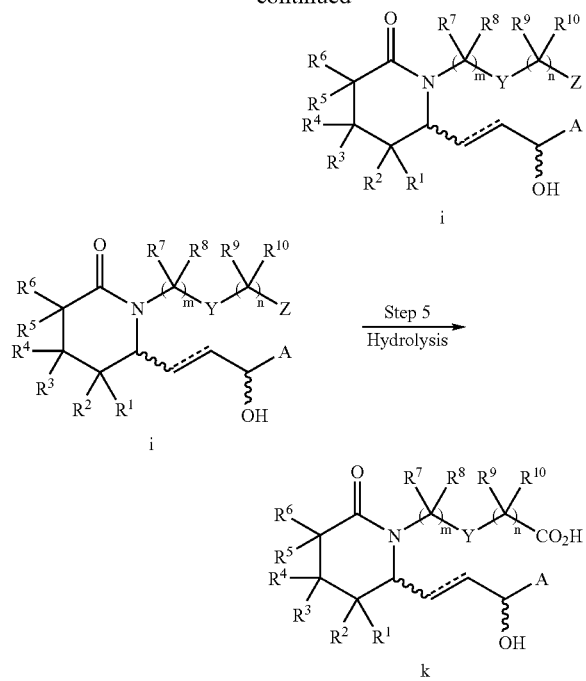

In step 1 of Scheme B, an N-alkylation of the lactam nitrogen of the protected alcohol c from Scheme A occurs. This alkylation may be effected by treatment of the protected alcohol c with a base such as sodium hydride or potassium hexamethyldisilazide at reduced temperature under inert atmosphere, followed by reaction with alkylating agent e. The resulting alkylated product (not shown) is then deprotected by treatment with acid to provide alcohol d. The leaving group LG may comprise a halo, tosyl or other suitable leaving group. The group U in Scheme B may be a protected alcohol (—O-PG) or may be $R^9R^{10}C_nZ$.

In step 2, the alcohol e of step 1 is oxidized to an aldehyde (not shown) by mild oxidation with the combination of dimethylsulfoxide and oxalyl chloride, Dess-Martin periodinane, the combination of TEMPO and sodium hypochlorite, PCC, PDC or the like. The aldehyde is immediately reacted with a phosphonic acid dialkyl ester compound g in the presence of base under polar aprotic conditions to give an enone condensation product f.

In step 3, the condensation product f of step 5 may optionally undergo reduction of the carbonyl and/or unsaturation present in the compound f, to provide a compound h. Stereoselective reduction of the carbonyl group of compound f using the "CBS" reagents as described by E. J. Corey, et al., *J. Am. Chem. Soc.* 1987, 109, 7925-7926 or other stereoselective reducing agent may be utilized in this step. If the preferential formation of one of the diastereomers is desired such as the S-hydroxyl isomer of Formula I when A is alkyl, arylalkyl, cycloalkylalkyl, or aryloxyalkyl, the stoichiometric combination of lithium aluminum hydride-ethanol-(S)-(−)-binaphthol as described by R. Noyori, et al, *J. Am. Chem. Soc.* 1984, 106, 6717-6725 can be used; or if the R-hydroxyisomer is desired, the combination of catalytic amounts of (R)-2-methyl-"CBS"-oxazaborolidine with stoichiometric borane-dimethyl sulfide as described by E. J. Corey, et al., *J. Am. Chem. Soc.* 1987, 109, 7925-7926; or stoichiometric amounts of (R)-3-pinanyl-9-borabicyclo[3.3.1]nonane as described by M. M. Midland et al., *J. Am. Chem. Soc.* 1980, 102, 867-869 is used. 1,2 Reduction may be effected with a hydride such as sodium borohydride, for example, in a solvent such as dichloromethane, toluene, ethanol, or tetrahydrofuran. The combination of a lanthanide salt such as cerium (III) chloride with sodium borohydide may also be used when A is aryl or heteroaryl. Catalytic hydrogenation of the double bond with Raney Ni or Pd on carbon yields a saturated side chain.

In step 4, homologation of compound h occurs wherein the group U is displaced by reaction with nucleophilic compound j to yield compound i. Where Z is a carboxylate, hydrolysis to the corresponding acid k may optionally be carried out by procedures well known by the artisan, such as addition of a base such as lithium, sodium of potassium hydroxide, or an acid such as sulfuric acid or hydrochloric acid in a protic or ethereal solvent containing water, or by employing a Lipase type VII in 0.05 M aqueous phosphate buffer at pH 6.8 as described by C. Luthy, et al. *J. Am. Chem. Soc.* 1978, 100, 6211-6217.

Many variations on the procedure of Scheme B may be used. For example, in certain embodiments the delta lactam c may be N-alkylated in step 1, and the N-alkylated lactam may then subsequently be converted to an aldehyde an then alkylated and selectively reduced to provide a compound of Formula I. In another variation, enone f may be reacted with a metal or a magnesium halide of general formula $R^{11}M$ where $R^{11}$ is alkyl, to introduce an additional group to the carbon attached to group A. Other variations on Scheme B are possible and will suggest themselves to those skilled in the art. Where necessary, conventional protecting group schemes may be used in association with groups A, Y and Z.

Another synthetic route to the subject compounds is shown in Scheme C below, that is preferred for embodiments wherein n is 0, Y is aryl or heteroaryl, and A, X, Z, $R^1$, $R^2$, $R^4$, $R^6$, $R^7$, $R^8$, $R^9$ and $R^{10}$ are as defined herein.

SCHEME C

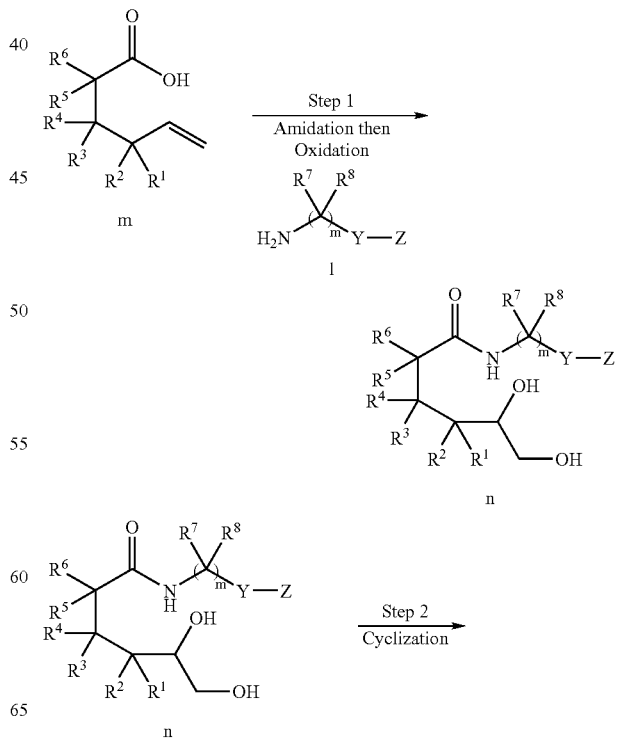

-continued

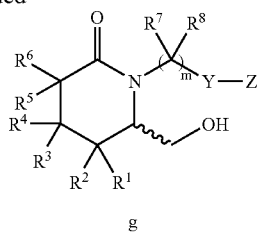

g

In step 1 of Scheme C, a 5-hexenoic acid m is reacted with an amine l and then subject to dihydroxylation of its double bond, to form amide n. 5-Hexenoic acids usable in step 1 are commercially available or can be prepared by well-known techniques.

The amide compound n is cyclized in step 2 to provide a delta lactam alcohol q. This cyclization process may be effected following protection of the primary hydroxyl of compound n. A suitable protecting agent such as t-butyldimethylsilyl trifluoromethanesulfonate or benzyl 2,2,2-trichloroacetimidate will, respectively, furnish the silyl or benzyl ether protecting groups. The secondary hydroxyl of n may then be activated for displacement by treatment with alkyl or aryl sulfonyl chloride such as methanesulfonyl chloride. The amide-secondary sulfonate (not shown) may then be treated with a base such as an alkali metal hydride or alkoxide in a polar medium such as methanol, tetrahydrofuran, or N,N-dimethylformamide to effect the cyclization. The pendent primary ether may be deprotected by the action of fluoride (tetrabutylammonium fluoride) in the case a silyl ether or catalytic hydrogenolysis (Pd—C under hydrogen gas) in the case of a benzyl ether. Compound q may then be processed according to Scheme B, Steps 2-5, to afford compounds of Formula I. If the R-enantiomer of q were desired, asymmetric dihydroxylation, according to M. Shipman, et al. *Synthesis* 1998, 1141-1144, may be used.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 0.001-50 mg daily, preferably 0.005-10 mg daily, and most preferably 0.010-1.0 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, pre-determined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in the Examples below.

Utility:

The compounds of the present invention are selective $EP_4$ prostaglandin agonists and may be used to treat several disease states associated with prostaglandin $EP_4$ receptor-mediated diseases, particularly for disease states associated with bone disorders, characterized by low bone mass and deterioration of bone tissue, with a consequent increase in bone fragility and susceptibility to fracture, especially those that require a significant increase in bone mass, bone volume, or bone strength. Conditions associated with low bone mass refer to a condition where the level of bone mass is below the age specific normal. Childhood idiopathic and primary osteoporosis are also included. Included in the treatment of osteoporosis is the prevention or attenuation of long term complications such as curvature of the spine, loss of height, prosthetic surgery, fracture healing and prevention of prostate malfunctioning. Also included is the treatment of bone loss associated with periodontitits or prosthetic ingrowth. Those skilled in the art will recognize that the term bone mass actually refers to bone mass per unit area which is sometimes referred to as bone mineral density. It has been discovered that the 8-aza-11-deoxy prostaglandin analogs of the present invention are useful for treating bone disorders. The subject compounds are also useful in the treatment of immunological diseases (autoimmune diseases, organ transplantation, etc.), asthma, neuronal cell death, thrombosis and stroke, hepatopathy, abortion, male and female sexual dysfunction, premature birth, inflammation such as rheumatoid arthritis, retina neuropathy disorders such as glaucoma, hypertension, female fertility disorder, blood clotting disorder, renal disfunction, dry eye, ichthyosis, elevated intraocular pressure, sleep disorders, gastric ulcer, preterm labor, dysmenorrhea, preeclampsia, eclampsia, or eosinophil disorder.

EXAMPLES

The following preparations and examples are given to enable those skilled in the art to more clearly understand and to practice the present invention. They should not be considered as limiting the scope of the invention, but merely as being illustrative and representative thereof.

Preparation 1

(4-Cyclopropyl-2-oxo-butyl)phosphonic Acid Dimethyl Ester

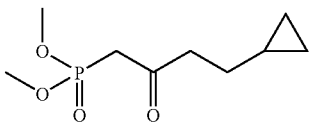

A suspension of sodium hydride (Aldrich, 95%, 760 mg, 31.6 mmol) in anhydrous tetrahydrofuran (90 mL) at ambient temperature was treated with dimethyl(2-oxo-propyl)phosphonate (Sigma, 5.0 g, 30.6 mmol) in tetrahydrofuran (10 mL) over 40 minutes and then cooled to 0° C. The suspension was treated with normal butyllithium (2.5 M in hexanes, 13.2 mL, 33 mmol) and the resulting solution was stirred at 0° for 2 hours. Bromocyclopropane (3.1 mL, 32 mmol) was added in tetrahydrofuran (10 mL) and the mixture was stirred at 0° for 1.5 hours and ambient temperature for 1 hour and then treated with ethanol (2 mL). The mixture was partitioned between 0.3 M aqueous HCl (150 mL) and dichloromethane (2×100 mL). The combined organic extracts was washed with brine and stored over anhydrous sodium sulfate. (4-Cyclopropyl-2-oxo-butyl)phosphonic acid dimethyl ester (2.11 g) was obtained after silica gel chromatography, eluted with 2:1 ethyl acetate: hexane as an oil: $^1$H NMR (300 MHz, CDCl$_3$) δ 3.74 (d, J=11.4 Hz, 6 H), 3.06 (d, J=22.8 Hz, 2 H), 2.67 (t, J=7.2 Hz, 2 H), 1.43 (q, J=7.2 Hz, 2 H), 0.61-0.72 (m, 1 H), 0.35-0.42 (m, 2 H), −0.03-0.08 (m, 2 H); $^{13}$C NMR (75 MHz, CDCl$_3$) δ 202.0 (d, J=6.0 Hz), 53.1 (d, J=6.3 Hz), 44.2, 41.4 (d, J=128 Hz), 28.6, 10.3, 4.5.

Preparation 2

{2-[3-(3-Fluorophenoxy)-phenyl]-2-oxo-ethyl}phosphonic acid dimethyl ester

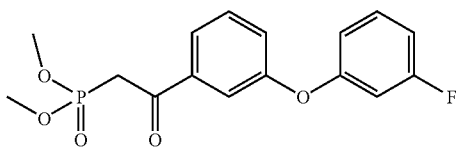

Step 1:

3-(3-Fluorophenoxy) benzoic acid methyl ester

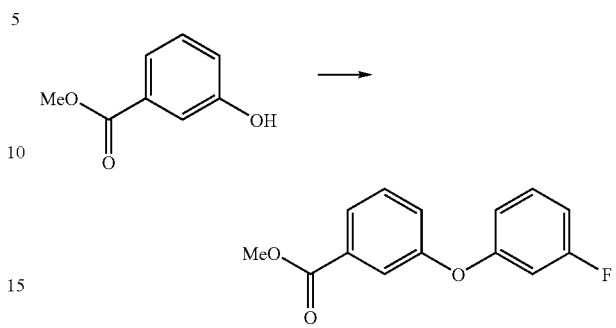

A suspension of methyl 3-hydroxybenzoic acid (5.4 g, 35.5 mmol), 3-fluorophenylboronic acid (5.5 g, 35.5 mmol), cupric acetate (7.1 g, 35.5 mmol), 3 Å molecular sieves (9 g), pyridine (12 mL, 145 mmol) in dichloromethane (220 mL) was stirred at ambient temperature under ambient atmosphere. After 11 days, the mixture was filtered through Celite® and the volatiles were removed from the filtrate. The 3-(3-fluorophenoxy)benzoic acid methyl ester (3.68 g) was eluted from silica gel column with 5:1 hexane:ethyl acetate and taken onto the next step.

Step 2

{2-[3-(3-Fluorophenoxy)-phenyl]-2-oxo-ethyl}phosphonic acid dimethyl ester

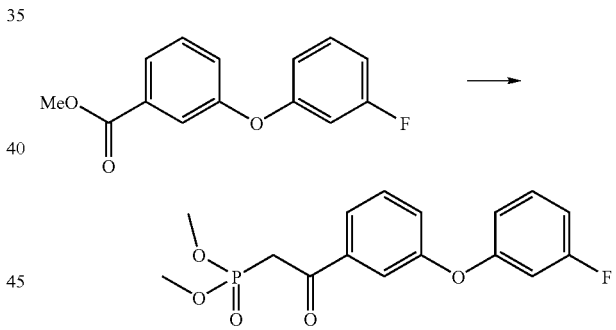

A tetrahydrofuran (100 mL) solution of dimethyl methylphosphonate (4.0 mL, 37.5 mmol) was cooled to −78° C. under argon and treated with normal butyllithium (15.0 mL, 2.5 M hexane solution, 37.5 mmol) and allowed to stir for 45 minutes. The ester obtained from step 1 (4.62 g, 18.7 mmol) was dissolved in tetrahydrofuran (15 mL) and added to the solution above at −78° C. and the resulting mixture was stirred at 0° C. for 1 hour. At which time, the yellow solution was partitioned between aqueous ammonium chloride (100 mL) and ethyl ether (200 mL). The organic portion was washed with fresh water (3×30 mL), then brine, and stored over anhydrous sodium sulfate. Following filtration and removal of the volatiles in vacuo, the desired β-ketophosphonate (5.8 g) was obtained as a viscous oil: $^1$H NMR (300 MHz, CDCl$_3$) δ 7.78 (dt, J=0.6, 0.9, 7.8 Hz, 1 H), 7.63 (t, J=2.1 Hz, 1 H), 7.48 (t, J=8.1 Hz, 1 H), 7.32-7.26 (m, 2 H), 6.90-6.78 (m, 2 H), 6.70 (dt, J=2.4, 9.9 Hz, 1 H), 3.80 (d, J=11.2 Hz, 6 H), 3.61 (d, J=22.6 Hz, 2 H).

Preparation 3

Methyl 4-[(2-chloroethyl)thio]butanoate

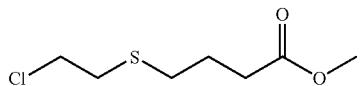

A 0° C. isopropanol (70 mL) solution of 4-mercaptobutyric acid (3.85 g, 20 mmol) was treated with sodium hydride in four portions (95%, 1.56 g total, 65 mmol) over 20 minutes and allowed to warm to room temperature. 1-Bromo-2-chloroethane (11 mL, 128 mmol) was added rapidly with the resulting suspension stirred vigorously for 2 days, then the volatiles were removed, and the residue was partitioned between 5% aqueous acetic acid and ethyl acetate. The combined organic extracts were washed with brine and stored over sodium sulfate. The extract was filtered and the volatiles were removed under vacuum. The residue was dissolved in methanol (60 mL) and cooled to 0° C. under argon atmosphere. Thionyl chloride (5 mL, 69 mmol) was added dropwise and the solution was stirred at room temperature. After 2-3 hours, the volatiles were removed, toluene was added, and the volatiles were removed again. Chromatography yielded (2.93 g, 14 mmol) of methyl 4-[(2-chloroethyl)thio]butanoate as a colorless oil: MS (NH$_3$) m/z 199 (M+1$^+$ with $^{37}$Cl), 197 (M+1$^+$ with $^{35}$Cl).

Example 1

6R-(1-Ethoxy-ethoxymethyl)-piperidin-2-one

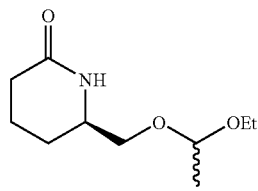

Step 1

6-Oxo-piperidine-2R-carboxylic acid methyl ester

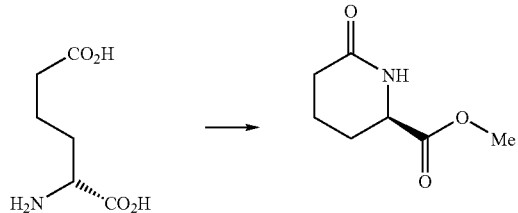

An acetic acid (30 mL) solution of R-2-aminoadipic acid (5 g, 31 mmol, Sigma Chemical Co.) was heated to reflux for six hours. Upon cooling, the volatiles were removed with a rotary evaporator and then with the aid of a toluene azeotrope (2×25 mL). The residue was dissolved in methanol (15 mL) and dichloromethane (30 mL) at ambient temperature. The solution was treated with a (trimethylsilyl)diazomethane (30 mL, 2 M in hexanes, Aldrich) and the golden solution was stirred for 4 hours. The solution was treated with drops of acetic acid until the golden color dissipated and the volatiles were removed with a rotary evaporator. The residue was loaded unto a pad of silica gel and washed with 1:1 dichloromethane and ethyl acetate. 6-Oxo-piperidine-2R-carboxylic acid methyl ester, eluted with ethyl acetate, was obtained as a tan oil (4.3 g): [α]$_D$+12.0° (c.1.0, CHCl$_3$) and the $^1$H NMR matched the literature report (C. E. Davies et al. *Synthetic Commun.* 1996, 26, 687-696.

Step 2:

6R-(1-Ethoxy-ethoxymethyl)-piperidin-2-one

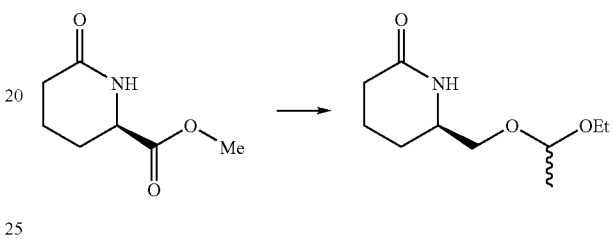

An ethanol (400 mL) solution of 6-oxo-piperidine-2R-carboxylic acid methyl ester (13.7 g, 87 mmol) was moderated with a tap-water bath under an Argon atmosphere and treated with sodium borohydride in three equal portions over 15 minutes (4.2 g, 109 mmol total). The reaction mixture was stirred for three hours at ambient temperature and then treated with acetic acid until an aliquot was about pH 4. The volatiles were removed with a rotary evaporator and the residue was loaded onto a pad of silica gel. 6R-Hydroxymethyl-piperidin-2-one was eluted with 5% methanol in dichloromethane and obtained as an oil. The oil (6.3 g, 49 mmol) was used directly by treatment with ethyl vinyl ether (7.0 mL, 73 mmol) and trifluoroacetic acid (1 mL) in dichloromethane (200 mL) at ambient temperature. After two hours, the solution was treated with aqueous sodium bicarbonate, extracted with dichloromethane (2×50 mL), and stored over anhydrous sodium sulfate. The 6R-(1-ethoxy-ethoxymethyl)-piperidin-2-one was obtained as an oil (6.9 g, 29 mmol) after filtration and removal of the volatiles: $^1$H NMR (300 MHz, CDCl$_3$) δ 6.14-6.24 (br.s, 1 H), 4.67-4.76 (m, 1 H), 3.18-3.67 (m, 5 H), 2.23-2.47 (m, 3 H), 1.64-1.98 (m, 3 H), 1.31 (dd, 3 H), 1.20 (dt, 3 H).

Example 2

4-{2-[(R)-2-((S)-(E)-5-Cyclopropyl-3-hydroxy-pent-1-enyl)-6-oxo-piperidin-1-yl]-ethylsulfanyl}-butyric acid

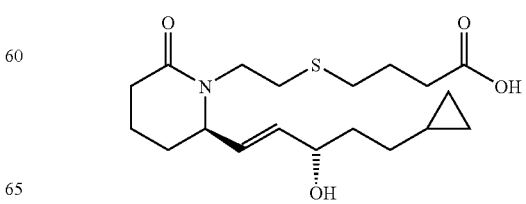

Step 1.

6R-Hydroxymethyl-1-(2-triisopropylsilanyloxy-ethyl)-piperidin-2-one

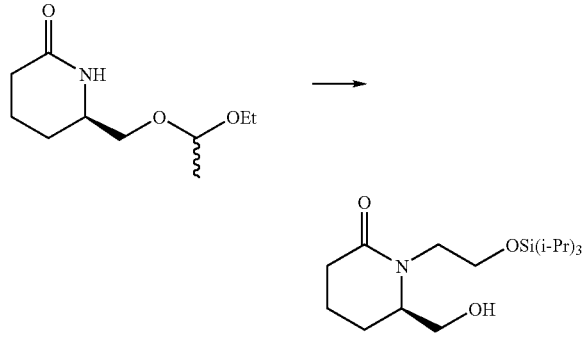

A dimethylformamide (70 mL) solution of 6R-(1-ethoxy-ethoxymethyl)-piperidin-2-one from Example 1 (6.9 g, 34 mmol) and potassium iodide (5.7 g, 34 mmol) was cooled to 0° C. under an Argon atmosphere. Sodium hydride (95%, 910 mg, 36 mmol) was added in one portion, and the bubbling mixture was allowed to warm to ambient temperature. After 1.5 hours, the mixture was treated with 2-bromoethanol tri-isopropylsilyl ether (10.5 g, 37.2 mmol) in dimethylformamide (15 mL) and warmed to 50° C. for 40 hours. The volatiles were removed by short-path distillation (5 mmHg, pot temperature to 75° C.) and the resulting pot residue was partitioned between water (100 mL) and 1:1 hexane:ethyl acetate (4×100 mL). The combined organic extracts was washed with water (2×25 mL) then brine and stored over anhydrous sodium sulfate. The solution was filtered and the volatiles were removed with a rotary evaporator.

The resulting tan oil (15.3 g) was directly treated with ethanol (150 mL) and pyridinium p-toluene sulfonic acid (800 mg, 3.2 mmol) and heated to reflux. After 60 minutes, the solution was cooled and treated with 5% aqueous sodium bicarbonate (20 mL) and the volatiles were removed with a rotary evaporator. The residue was loaded onto a pad of silica gel and washed with 2:1 ethyl acetate:hexane. 6R-Hydroxymethyl-1-(2-triisopropylsilanyloxy-ethyl)-piperidin-2-one (5.22 g, 15.8 mmol) was eluted with ethyl acetate: $[\alpha]_D$ −37.5° (c.1.0, CH$_3$CN); IR (cm$^{-1}$) 3373, 2943, 2865, 1617, 1465; $^1$H NMR (300 MHz, CDCl$_3$) δ 4.11-4.20 (m, 1 H), 3.61-3.90 (m, 5 H), 3.42-3.53 (m, 2 H), 2.36-2.41 (m, 2 H), 1.63-1.99 (m, 4 H), 1.07 (s, 21 H); $^{13}$C NMR (75 MHz, CDCl$_3$) δ 172.1, 64.8, 62.7, 61.0, 50.1, 32.8, 26.4, 18.7, 18.3, 12.2; MS (ES) m/z 330 (M$^{+1}$)$^+$.

Step 2.

6R-(5-Cyclopropyl-3-oxo-pent-1E-enyl)-1-(2-triisopropylsilanyloxy-ethyl)-piperidin-2-one

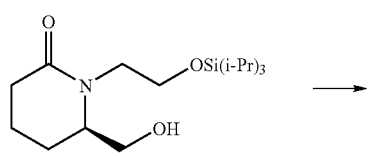

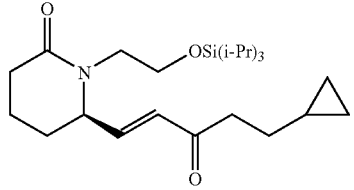

A −78° C. dichloromethane solution of anhydrous dimethyl sulfoxide (0.87 mL, 11.2 mmol) under an Argon atmosphere was treated with oxalyl chloride (2 M CH$_2$Cl$_2$ solution, 3.9 mL, 7.8 mmol), which was added over a 3 minute period. After 20 minutes, a dichloromethane (10 mL) solution of 6R-hydroxymethyl-1-(2-triisopropylsilanyloxy-ethyl)-piperidin-2-one from step 1 (1.85 g, 5.6 mmol) was added dropwise. The resulting yellow solution was stirred for 15 minutes at −78° and then treated rapidly with triethylamine (2.3 mL, 16.8 mmol), after which the cooling bath was removed. After 30 minutes, the suspension was poured into aqueous sodium bicarbonate and extracted with dichloromethane (3×50 mL). The combined organic extracts was stored over anhydrous sodium sulfate. The extract was filtered and the volatiles were removed to yield the aldehyde as a tan oil (1.75 g), which was used directly.

The crude aldehyde (875 mg, 2.65 mmol) was dissolved in acetonitrile (25 mL) and treated with (4-cyclopropyl-2-oxo-butyl)phosphonic acid dimethyl ester (670 mg, 3.05 mmol), lithium chloride (135 mg, 3.2 mmol), and diisopropylethylamine (0.51 mL, 2.9 mmol). After stirring the suspension at ambient temperature for 2.5 hours, it was poured into ether and aqueous ammonium chloride. The aqueous layer was extracted with ethyl acetate (4×30 mL) and stored over anhydrous sodium sulfate. The extract was filtered, volatiles removed in vacuo, and the residue subjected to silica gel chromatography. 6R-(5-Cyclopropyl-3-oxo-pent-1E-enyl)-1-(2-triisopropylsilanyloxy-ethyl)-piperidin-2-one (793 mg, 1.85 mmol) was obtained as an oil: $^1$H NMR (300 MHz, CDCl$_3$) δ 6.70 (dd, J=5.5, 15.8 Hz, 1 H), 6.11 (dd, J=0.6, 15.8 Hz, 1 H), 4.52-4.59 (m, 1 H), 4.06-4.14 (m, 1 H), 3.95 (dt, J=3.6, 9.3 Hz, 1 H), 3.71-3.80 (m, 1 H), 2.70-2.79 (m, 1 H), 2.66 (t, J=6.9 Hz, 1 H), 2.37-2.44 (m, 1 H), 1.96-2.05 (m, 1 H), 1.49-1.88 (m, 6 H), 1.05 (s, 22 H), 0.64-0.73 (m, 1 H), 0.39-0.44 (m, 2H), 0.02-0.07 (m, 2H).

Step 3.

6R-(5-Cyclopropyl-3S-hydroxy-pent-1E-enyl)-1-(2-hydroxyethyl)-piperidin-2-one

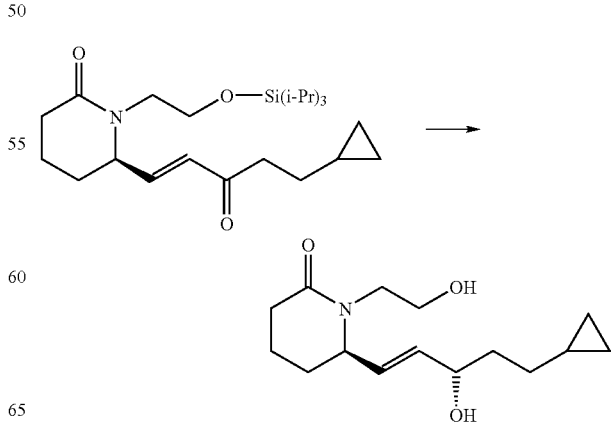

A 0° C. toluene (10 mL) solution of (R)-2-methyl-CBS-oxazaborolidine (0.20 mL, 1 M toluene solution from Aldrich) and borane dimethyl sulfide complex (0.26 mL, 1.3 mmol, 5 M ethyl ether solution) under an argon atmosphere was generated. 6R-(5-Cyclopropyl-3-oxo-pent-1E-enyl)-1-(2-triisopropylsilanyloxy-ethyl)-piperidin-2-one (793 mg, 1.85 mmol) was added in anhydrous toluene (5 mL) dropwise and stirred at 0° for 20 minutes. The solution was quenched with HCl (1.5 mL, 2 M solution in methanol) and the volatiles were removed in vacuo to yield a solid residue. The residue was redissolved in methanol and the volatiles were removed again in vacuo. The residue was loaded onto a column of silica gel and 6R-(5-cyclopropyl-3S-hydroxy-pent-1E-enyl)-1-(2-triisopropylsilanyloxy-ethyl)-piperidin-2-one (541 mg) was eluted with a gradient of 2-6% isopropanol in 3:1 hexane:ethyl acetate and used directly.

6R-(5-Cyclopropyl-3S-hydroxy-pent-1E-enyl)-1-(2-triisopropylsilanyloxy-ethyl)-piperidin-2-one (541 mg, 1.26 mmol) was dissolved in THF (10 mL) and treated with tetrabutylammonium fluoride hydrate (480 mg, 1.5 mmol). The solution was stirred for 2.5 h at room temperature, diluted with 10 mL hexane and loaded onto a pad of silica gel. 6R-(5-Cyclopropyl-3S-hydroxy-pent-1E-enyl)-1-(2-hydroxyethyl)-piperidin-2-one (328 mg, 1.23 mmol) eluted with 10% ethanol in ethyl acetate and obtained as an oil, $^1$H NMR (300 MHz, CDCl$_3$-D$_2$O, partial spectrum) δ 5.64-5.59 (m, 2 H), 4.22-4.18 (m, 1 H), 4.03-3.98 (m, 1 H), 3.80-3.69 (m, 3 H), 3.31-3.20 (m, 1 H), 0.72-0.61 (m, 1 H), 0.48-0.40 (m, 2 H), 0.08-0.00 (m, 2 H); MS: m/z 268 (M$^{+1}$)$^+$, 250 (M$^{+1}$ loss of H$_2$O)$^+$.

Step 4:

4-{2-[(R)-2-((S)-(E)-5-Cyclopropyl-3-hydroxy-pent-1-enyl)-6-oxo-piperidin-1-yl]-ethylsulfanyl}-butyric acid methyl ester

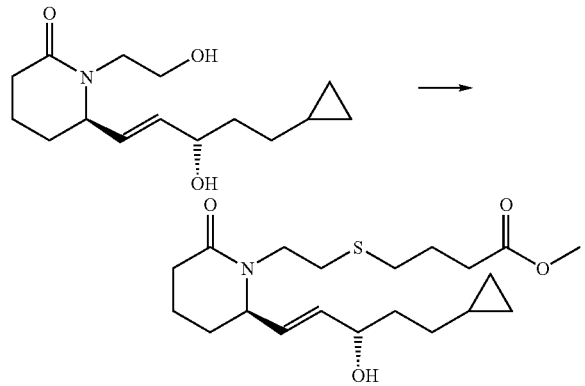

6R-(5-Cyclopropyl-3S-hydroxy-pent-1E-enyl)-1-(2-hydroxyethyl)-piperidin-2-one from step 3 (328 mg, 1.23 mmol) was dissolved in tetrahydrofuran (10 mL) and cooled to −20° C. under Argon. This solution was sequentially treated with triethylamine (0.21 mL, 1.48 mmol) and methanesulfonyl chloride (0.095 mL, 1.23 mmol) which resulted in a suspension. In a separate vessel, a solution of anhydrous methanol (1 mL) and anhydrous tetrahydrofuran (5 mL) under an argon atmosphere was treated with potassium t-butoxide (3.7 mL, 1 M tetrahydrofuran solution, Aldrich) and the slightly warm solution was stirred for 10 minutes. γ-Thiobutyrolactone (0.26 mL, 3.1 mmol, Aldrich Chemical Co.) was added in one portion and stirred at ambient temperature for 10 minutes and the suspension of the mesylate was added via cannula to the potassium thiolate solution. The mixture was stirred for 18 hours at ambient temperature and then partitioned between aqueous ammonium chloride and ethyl acetate (4×25 mL). The combined organic extracts were stored over anhydrous sodium sulfate, and the volatiles were removed with a rotary evaporator. The resulting 4-{2-[(R)-2-((S)-(E)-5-cyclopropyl-3-hydroxy-pent-1-enyl)-6-oxo-piperidin-1-yl]-ethylsulfanyl}-butyric acid methyl ester (98 mg, 0.25 mmol) was obtained following elution from silica gel chromatography with 4:1 ethyl acetate:hexane as an oil: $^1$H NMR (300 MHz, CDCl$_3$) δ 5.58-5.64 (m, 2 H), 4.16-4.22 (m, 1 H), 4.02-4.07 (m, 1 H), 3.87-3.98 (m, 1 H), 3.68 (s, 3 H), 2.95-3.04 (m, 1 H), 2.63-2.76 (m, 2 H), 2.58 (t, J=7.2 Hz, 2 H), 2.44 (t, J=7.2 Hz, 2 H), 2.34-2.41 (m, 2 H), 1.58-1.99 (m, 9 H), 1.22-1.30 (m, 2 H), 0.61-0.72 (m, 1 H), 0.40-0.47 (m, 2 H), 0.02-0.07 (m, 2 H).

Step 5.

4-{2-[(R)-2-((S)-(E)-5-Cyclopropyl-3-hydroxy-pent-1-enyl)-6-oxo-piperidin-1-yl]-ethylsulfanyl}-butyric Acid

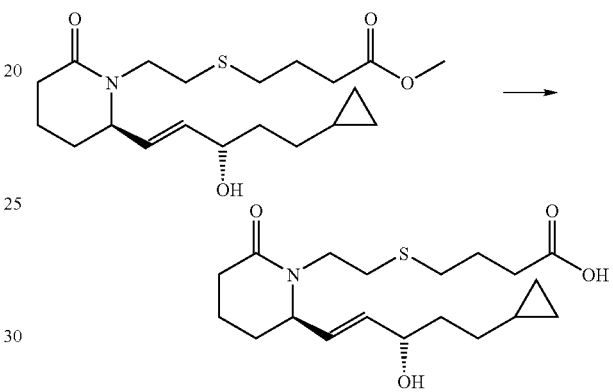

A methanol (10 mL) solution of 4-{2-[(R)-2-((S)-(E)-5-Cyclopropyl-3-hydroxy-pent-1-enyl)-6-oxo-piperidin-1-yl]-ethylsulfanyl}-butyric acid methyl ester from step (4, 98 mg, 0.25 mmol) was treated with sodium hydroxide (0.3 mL, 5 M aqueous) and stirred at ambient temperature for 3 hours. The volatiles were removed under a stream of nitrogen and the mixture was partitioned between water and ethyl ether. The aqueous layer was rendered acidic with hydrochloric acid (12 M aqueous) and extracted with ethyl acetate (3×15 mL). The combined organic extracts was stored over anhydrous sodium sulfate. 4-{2-[(R)-2-((S)-(E)-5-Cyclopropyl-3-hydroxy-pent-1-enyl)-6-oxo-piperidin-1-yl]-ethylsulfanyl}-butyric acid (94 mg, 0.25 mmol) was obtained following filtration and removal of the volatiles as an oil: $^1$H NMR (300 MHz, CDCl$_3$) δ 6.7 (br.s, 1 H), 5.58-5.63 (m, 2 H), 4.18-4.22 (m, 1 H), 4.02-4.07 (m, 1 H), 3.87-3.98 (m, 1 H), 2.98-3.08 (m, 1 H), 2.62-2.72 (m, 2 H), 2.59 (t, J=6.9 Hz, 2 H), 2.36-2.49 (m, 4 H), 1.61-1.99 (m, 8 H), 1.22-1.30 (m, 2 H), 0.59-0.71 (m, 1 H), 0.40-0.46 (m, 2 H), 0.00-0.06 (m, 2 H); MS: m/z M$^{+1}$, 370.

Using the procedure of Example 2, the following compounds of formula I were prepared with the following adaptations.

4-(2-{2R-[3R-(4'Chloro-2'methylbiphenyl-3-yl)-3-hydroxy-propyl]-6-oxo-piperidin-1-yl}-ethylsulfanyl) butyric acid was prepared by use of [2-(4'chloro-2'-methyl-biphen-3-yl)-2-oxo-ethyl] phosphonic acid dimethyl ester in step 2; in step 3, the enone was exposed to 1 atm of hydrogen gas with a catalytic amount of 10% Pd—C for 1.5 hours followed by treatment with (S)-2-methyl-CBS with borane-dimethyl sulfide at 0° C.: MS: m/z M$^{+1}$, 504 and 506.

7-{2R-[3S-Hydroxy-4-(4-hydroxy-3-methyl-phenyl)-but-1E-enyl]-6-oxo-piperidin-1-yl} heptanoic acid was prepared by the use of 3-[(4-hydroxy-3-methyl-phenyl)-2-oxo-propyl] phosphonic acid dimethyl ester in step 2 and the exclusion of step 4: MS: m/z M$^{+1}$, 404.

7-{2R-[3S-Hydroxy-4-(3-methoxymethyl-phenyl)-but-1E-enyl]-6-oxo-piperidin-1-yl} heptanoic acid was prepared by the use of 3-[(3-methoxymethyl-phenyl)-2-oxo-propyl] phosphonic acid dimethyl ester in step 2 and the exclusion of step 4: MS: m/z M$^{+1}$, 418.

7-{2R-[3S-Hydroxy-4-(4-hydroxy-3-isopropyl-phenyl)-but-1E-enyl]-6-oxo-piperidin-1-yl} heptanoic acid was prepared by the use of 3-[(3-hydroxy-3-isopropyl-phenyl)-2-oxo-propyl] phosphonic acid dimethyl ester in step 2 and the exclusion of step 4: MS: m/z M$^{+1}$, 432.

4-(2-{2R-[3-Hydroxy-3-(1-phenylcyclopropyl)-prop-1E-enyl]-6-oxo-piperidin-1-yl}ethylsulfanyl) butyric acid was prepared by the use of 2-(phenylcyclopropyl)-2-oxo-ethyl] phosphonic acid dimethyl ester in step 2 and use of the combination cerium(III) chloride and sodium borohydride in step 3 instead of the stereoselective "CBS" conditions: MS: m/z M$^{+1}$, 418.

4-(2-{2R-[3R-3-Hydroxy-3-(trifluoromethyl-furan-2-yl)-propyl]-6-oxo-piperidin-1-yl}-ethylsulfanyl) butyric acid was prepared by the use of 2-[(5-trifluoromethylfuran-2-yl)-2-oxo-ethyl] phosphonic acid dimethyl ester in step 2; in step 3 the enone was exposed to 1 atm of hydrogen gas with a catalytic amount of 10% Pd—C for 1.5 hours followed by treatment with (S)-2-methyl-CBS with borane-dimethyl sulfide at 0° C.: MS: m/z M$^{+1}$, 438.

4-(2-{2R-[3R-Hydroxy-3-(1-phenylcyclopropyl)-propyl]-6-oxo-piperidin-1-yl}ethylsulfanyl) butyric acid was prepared by the use of 2-[(phenylcyclopropyl)-2-oxo-ethyl] phosphonic acid dimethyl ester in step 2; in step 3 the enone was exposed to 1 atm of hydrogen gas with a catalytic amount of 10% Pd—C for 1.5 hours followed by treatment with (S)-2-methyl-CBS with borane-dimethyl sulfide at 0° C.: MS: m/z M$^{+1}$, 420.

4-(2-{2R-[3S-Hydroxy-4-(3-methoxymethyl-phenyl)-but-1E-enyl]-6-oxo-piperidin-1-yl}ethylsulfanyl) butyric acid was prepared by the use of 3-[(3-methoxymethylphenyl)-2-oxo-propyl] phosphonic acid dimethyl ester in step 2: MS: m/z M$^{+1}$, 436.

7-{2R-[3R-(4'-Hydroxy-2'-methylbiphenyl-3-yl)-3-hydroxy-propyl]-6-oxo-piperidin-1-yl} heptanoic acid was prepared by use of 2-(4'-hydroxy-2'-methyl-biphen-3-yl)-2-oxo-ethyl] phosphonic acid dimethyl ester in step 2; in step 3, the enone was exposed to 1 atm of hydrogen gas with a catalytic amount of 10% Pd—C for 1.5 hours followed by treatment with (S)-2-methyl-CBS with borane-dimethyl sulfide at 0° C.; and the exclusion of step 4: MS: m/z M$^{+1}$, 468.

7-{2R-[3-Hydroxy-3-(4'-hydroxy-2'methylbiphenyl-3-yl)-prop-1E-enyl]-6-oxo-piperidin-1-yl} heptanoic acid was prepared by the use of [2-(4'-hydroxy-2'-methyl-biphen-3-yl)-2-oxo-ethyl] phosphonic acid dimethyl ester in step 2; in step 3 the combination of cerium(III) chloride and sodium borohydride at 0° C.; and the exclusion of step 4: MS: m/z M$^{+1}$, 466.

7-(2-{2R-[3R-(4'-Hydroxy-2'methylbiphenyl-3-yl)-3-oxo-propyl]-6-oxo-piperidin-1-yl} heptanoic acid was prepared by the use of [2-(4'-hydroxy-2'-methyl-biphen-3-yl)-2-oxo-ethyl] phosphonic acid dimethyl ester in step 2; in step 3 the enone was exposed to 1 atm of hydrogen gas with a catalytic amount of 10% Pd—C for 2 hours; and the exclusion of step 4: MS: m/z M$^{+1}$, 466.

4-{2-[2R-(5-Cyclobutyl-3S-hydroxy-pent-1E-enyl)-6-oxo-piperidin-1-yl]ethylsulfanyl} butyric acid was prepared by the use of (4-cyclobutyl-2-oxo-butyl)phosphonic acid dimethyl ester in step 2: MS: m/z M$^{+1}$, 384.

4-(2-{2R-[3R-(3'-fluorophenoxy-phenyl-3-yl)-3-hydroxy-propyl]-6-oxo-piperidin-1-yl}-ethylsulfanyl) 3-methyl-butyric acid was prepared by use of [2-(3-fluorophenoxy-phen-3-yl)-2-oxo-ethyl] phosphonic acid dimethyl ester in step 2; in step 3, the enone was exposed to 1 atm of hydrogen gas with a catalytic amount of 10% Pd—C for 1.5 hours followed by treatment with (S)-2-methyl-CBS with borane-dimethyl sulfide at 0° C.; and the use of methyl 4-mercapto-3-methyl butyrate in step 4 instead of γ-thiolactone: MS: m/z M$^{+1}$, 504.

4-{2-[2R-(3-Hydroxy-4,4-dimethyl-oct-1E-enyl)-6-oxo-piperidin-1-yl]-ethylsulfanyl} butyric acid was prepared by the use of (3,3-dimethyl-2-oxo-heptyl) phosphonic acid dimethyl ester in step 2; and the combination of cerium (III) chloride with sodium borohydride in step 3: MS: m/z M$^{+1}$, 400.

7-{2R-[3-Hydroxy-3-(2,5-dimethylphenyl-3-yl)-prop-1E-enyl]-6-oxo-piperidin-1-yl} heptanoic acid was prepared by the use of [2-(2,5-dimethyl-phen-3-yl)-2-oxo-ethyl] phosphonic acid dimethyl ester in step 2; in step 3 the combination of cerium (III) chloride and sodium borohydride at 0° C.; and the exclusion of step 4: MS: m/z M$^{+1}$, 388.

7-[-2R-(3-Hydroxy-4-phenoxy-but-1E-enyl)-6-oxo-piperidin-1-yl] heptanoic acid was prepared by the use of (3-phenoxy-2-oxo-propyl) phosphonic acid dimethyl ester in step 2; in step 3 the combination of cerium (III) chloride and sodium borohydride at 0° C.; and the exclusion of step 4: MS: m/z M$^{+1}$, 390.

7-{2R-[3-Hydroxy-3-(3'chloro-biphenyl-3-yl)-prop-1E-enyl]-6-oxo-piperidin-1-yl} heptanoic acid was prepared by the use of [2-(3'-chloro-biphen-3-yl)-2-oxo-ethyl] phosphonic acid dimethyl ester in step 2; in step 3 the combination of cerium(III) chloride and sodium borohydride at 0° C.; and the exclusion of step 4: MS: m/z M$^{+1}$, 470 and 472.

7-{2R-[3R-(3'chloro-biphenyl-3-yl)-3-hydroxy-propyl]-6-oxo-piperidin-1-yl} heptanoic acid was prepared by the use of [2-(3'-chloro-biphen-3-yl)-2-oxo-ethyl] phosphonic acid dimethyl ester in step 2; in step 3 the enone was exposed to 1 atm of hydrogen gas with a catalytic amount of 10% Pd—C for 2 hours followed by the use the (S)-2-methyl-CBS with borane at 0° C.; and the exclusion of step 4: MS: m/z M$^{+1}$, 472 and 474.

Example 3

4-(2-{2-[3-Hydroxy-4-(3-trifluoromethyl-phenyl)-but-1E-enyl]-6-oxo-piperidin-1-yl}-ethyl) benzoic acid

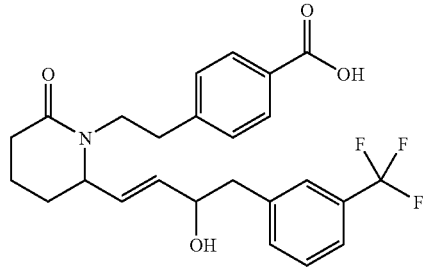

Step 1

4-[2-(5,6-Dihydroxy-hexanoylamino)-ethyl] benzoic acid methyl ester.

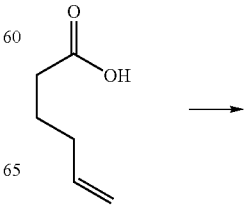

-continued

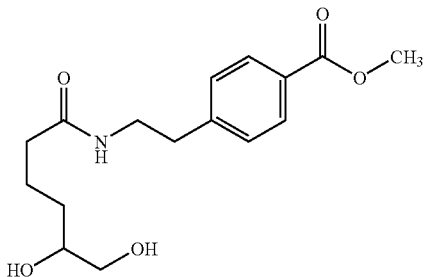

A N,N-dimethylformamide (110 mL) solution of 5-hexenoic acid (8.45 g, 73.8 mmol, Aldrich) was treated with carbonyl diimidazole (12 g, 74 mmol) was heated to 50° C. for 3 hours. The solution was cooled, treated with diisopropylethyl amine (18.4 mL, 105 mmol) and methyl 4-(2-aminoethyl)benzoate (12.6 g, 70.3 mmol, prepared according to T. Takemoto, et al. European Patent Application 0544205 to Ajinomoto Co.), and heating resumed at 50° for 3 additional hours. The mixture was partitioned between water (400 mL) and ethyl acetate (3×150 mL). The combined organic extracts was washed with 1 M HCl, saturated NaHCO$_3$, and brine and stored over anhydrous MgSO$_4$. The extract was filtered and the volatiles were removed in vacuo. A solid (11.4 g) was obtained and was used directly dissolved in acetone (440 mL) and water (10 mL). This solution was treated with N-methyl morpholine N-oxide (5.35 g, 45.7 mmol), osmium tetraoxide (approx. 20 mg), and heated to reflux for 3 hours. The alkene had been consumed by TLC and the mixture was cooled and treated with aqueous solution on sodium bisulfite and rendered acidic with 1 M aqueous HCl. 4-[2-(5,6-Dihydroxy-hexanoylamino)-ethyl] benzoic acid methyl ester (12.85 g) was obtained as solid following extraction with chloroform (3×200 mL), storage over anhydrous sodium sulfate, removal of the volatiles, and recrystallization from ethyl acetate and a minor volume of methanol.

Step 2.

4-[2-(2-Hydroxymethyl-6-oxo-piperdin-1-yl)-ethyl] benzoic acid methyl ester

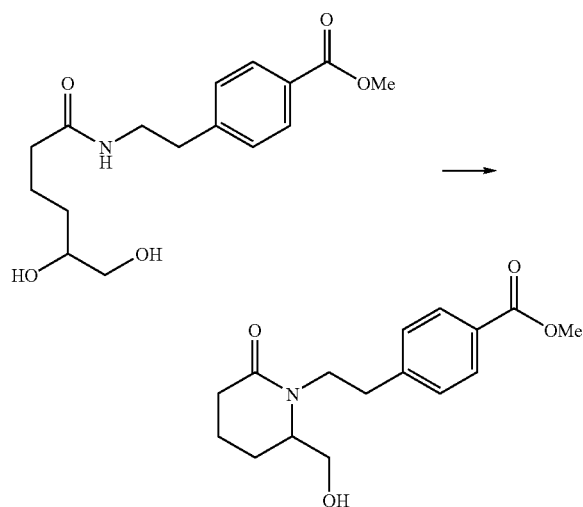

A 0° C. dichloromethane (170 mL) and DMF (35 mL) solution of 4-[2-(5,6-dihydroxy-hexanoylamino)-ethyl]benzoic acid methyl ester (7.4 g) was treated with 2,6-lutidine (9.1 mL), and t-butyldimethylsilyl trifluoromethanesulfonate (5.5 mL) and then stirred overnight. The mixture was partitioned between aqueous sodium bicarbonate and ethyl acetate (3×150 mL). The desired primary silyl ether (5.8 g) was isolated, following drying and evaporation of the volatiles with rotary evaporator, by silica gel chromatography elution with 2:1 hexanes:ethyl acetate. The ether (5.85 g) was dissolved in dichloromethane (50 mL) and triethyl amine (3.85 mL) and cooled to 0° C. under an Argon atmosphere. The solution was treated with methanesulfonyl chloride (1.5 mL, 19.3 mmol) and stirred for 30 minutes, whereupon it poured into aqueous sodium bicarbonate. The desired secondary sulfonate (6.6 g) was obtained following extraction with dichloromethane (3×30 mL), drying over anhydrous sodium sulfate and removal of the volatiles in vacuo and used directly in the next operation. The crude secondary sulfonate (6.6 g, 13.2 mmol) was dissolved in anhydrous toluene (106 mL) at ambient temperature under Argon and treated with potassium t-butoxide (1 M, THF solution from Aldrich). After 2 hours, the brown mixture was partitioned between aqueous ammonium chloride and ethyl acetate (4×50 mL) and the combined organic extracts was stored over anhydrous sodium sulfate. The desired lactam (1.79 g, 4.6 mmol) was isolated by silica gel chromatography (eluent: 4:1 hexanes:ethyl acetate) and directly dissolved in tetrahydrofuran (23 mL). The solution was treated with tetrabutylammonium fluoride hydrate (1.74 g, 5.5 mmol) and stirred at rt for 1 hour. 4-[2-(2-Hydroxymethyl-6-oxo-piperdin-1-yl)-ethyl]benzoic acid methyl ester (1.055 g) was obtained following filtration through a pad of silica, washed with 1:1 ethyl acetate:hexane.

4-(2-{2-[3-Hydroxy-4-(3-trifluoromethyl-phenyl)-but-1E-enyl]-6-oxo-piperidin-1-yl}-ethyl) benzoic acid was prepared from 4-[2-(2-hydroxymethyl-6-oxo-piperdin-1-yl)-ethyl] benzoic acid methyl ester according to Example 2 by employing 4-[(3-trifluoromethyl-phenyl)-2-oxo-butyl] phosphonic acid dimethyl ester (prepared according to Preparation 2) in step 2, and sodium borohydride in step 3, and excluding step 4: MS: m/z M$^{+1}$, 462.

According to Example 3,4-(2-{2-[3-(4'chloro-2'-methyl-biphen-3-yl)-3-hydroxy-propyl]-6-oxo-piperidin-1-yl}-ethyl)benzoic acid was prepared with the following changes. In step 2, the [3-(4'chloro-2'-methyl-biphen-3-yl)-2-oxo-propyl] phosphonic acid dimethyl ester (prepared according to Preparation 2) was used, in step 3 the double was reduced under 1 atm hydrogen gas at ambient temperature with a catalytic amount of 10% Pd—C in ethyl acetate followed by treatment with sodium borohydride, and step 4 was excluded: MS: m/z M$^{+1}$, 507 and 509.

Example 4

Formulations

Pharmaceutical preparations for delivery of the subject compounds by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
| --- | --- |
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
| --- | --- |
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
| --- | --- |
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 5

Functional Activity of $EP_4$ (or $EP_2$) Receptor by a Luciferase Assay a. Generation of Stably Transfected EP4-Luciferase Clones Prostanoid receptor EP4 cDNA corresponding to the full-length coding sequence was subcloned into the appropriate sites of the mammalian expression vector pcDNA 3.1(+)/Zeo (Invitrogen). In addition, the sequence containing CAMP responsive element (CRE) and luciferase gene was cloned to a pXP1 vector. The co-transfection to the CHO cells with EP4R containing pcDNA and CRE-luciferase containing pXP1 were carried out with a DNA ratio of 5 to 1 by Fugene (Roche Molecular) in a F-12 media (Gibco) supplemented with 10% heat inactivated fetal Bovine Serum (Gibco). Three days after the transfection, the culture was replace with fresh media containing Zeocin. The culture was maintained for one month until stable clones were generated.

b. c-AMP Dependent luciferase gene assay

The functional activity of an EP4 agonistic ligand upon its binding to the receptor was measured by the production of intra-cellular c-AMP. Here the level of c-AMP was measured indirectly by the translation of a reporter gene, luciferase in the EP4-luciferase clones. The cells of EP4-luciferase clone were subcultured in 200 ul of F12 (Gibco, BRL) media containing 10% FBS (Gibco, BRL), and 25 mM Hepes to 96-well plates (Packard) at the density of 40,000 cells/well. After an overnight culture at 37° C., 5% $CO_2$, 95% air, the culture media was removed in the next morning. The cells were washed twice with 100 ul of Hanks buffer, and re-furnished with 90 ul of F12 media containing 0.1% BSA. After pre-incubation of the culture for one and half to three hours at 37° C., 5% CO2, 95% air, 10 ul of compounds of interest at 10× of desired concentration were added to culture and the incubation at 37° C. was continued for another three hours. 0.1 uM of PGE2 as a full agonist control was routinely included to each assay to determine the maximal stimulation of luciferase mediated through EP4 receptor.

At the end of incubation, the culture media was dumped and blotted to dry. The plate was then ready to assay for luciferase.

c. Quantitation of luciferase activity

An assay kit, LucLite, purchased from Packard was used to quantitate luciferase activity. 30 minutes prior to end of incubation, LucLite substrate and substrate buffer (Packard) were allowed to equilibrate to room temperature. The substrate was dissolved in the substrate buffer and mixed by inversion. Equal volumes of Dulbecco's Phosphate Buffered Saline (DPBS, Gibco BRL) containing 1 mM $MgCl_2$ and 1 mM $CaCl_2$ were then mixed with the reconstituted substrate solution for use in the next step. 100 ul of the mixed solution was added to each well of the 96-well plate. The plate was shaken at 300 rpm on plate shaker for 3 min. The plate cover was removed and replaced with plate sealer (Packard) for counting in a scintillation counter. The EC50 of a compound was then determined by a four-parameter curvefit program of KaleidaGraph. Compounds of Formula I showed activity using the above assay.

Example 6

Competitive Binding Assay of $[^3H]PGE_2$ to $rEP_1$, $rEP_2$, $rEP_3$ and $rEP_4$ Receptor a. Cell Culture and Transfections Stably transfected cells expressing EP3 were grown in F-12 media (GIBCO) supplemented with 10% heat inactivated certified Fetal Bovine Serum (GIBCO) and pelleted. Prostanoid receptor EP2 or EP4 cDNA corresponding to the full-length coding sequence was subcloned into the appropriate sites of the mammalian expression vector pcDNA 3.1(+)/Zeo (Invitrogen). Transfection-scale quantities of the vector were prepared using the Qiagen Endo-Free Plasmid Maxi Kit and transfected into COS-7 cells using FuGene 6 (Roche Molecular) according to the manufacturer's instructions (Roche). COS-7 cells were grown in DMEM (GIBCO) supplemented with 10% heat inactivated certified Fetal Bovine Serum (GIBCO) and Gentamicin (GIBCO), and were harvested 72 hours after transfection. Cells were pelleted by centrifugation, washed with PBS (GIBCO), repelleted, then flash-frozen in dry-ice/Ethanol or used directly for membrane preparation.

b. Membrane Preparation

All procedures for membrane preparation were performed at 4° C. Prostanoid receptor-transfected COS-7 cells or stably transfected CHO cells were homogenized in assay buffers (see recipe, below) using a Polytron homogenizer (Brinkman) and centrifuged at 48,000× g for 30 minutes. Pellets were resuspended in assay buffer and resuspended by sonication using a Branson sonifier. Protein concentration was determined using the BioRad DC Protein Assay following the manufacturer's directions and stored at −80° C.

c. Prostanoid Receptor Binding Assays

Methods for competitive affinity binding assays of EP2, EP3 and EP4 were derived from those described in M. Abramovitz et al, "The utilization of recombinant prostanoid receptors to determine the affinities and selectivities of prostaglandins and related analogs" *Biochimica et Biophysica Acta* 1483 (2000) 285-293. Binding assays were performed in a final incubation volume of 0.2 mL in the following assay buffers: 20 mM HEPES, 1 mM EDTA, and 10 mM $MgCl2$ (pH 7.4) (EP3) or 10 mM MES, 10 mM $MnCl2$, and 1 mM EDTA (pH to 6.0 with NaOH) (EP2 and EP4) and radioligand {2.25 nM (EP3) or 2.5 nM (EP2) [3H]-$PGE_2$ (200 Ci/mmol, NEN)}. Reactions were initiated by addition of membrane protein (approximately 50 ug/reaction for EP3, 100 ug for EP2 and EP4). Dimethylsulfoxide (Sigma) concentration was kept constant at 1% (v/v) in all incubations, and compounds were assayed at final concentrations of 100 uM-0.3 nM. Non-specific binding was determined in the presence of 10 □M of non-radioactive $PGE_2$ (Cayman Chemical). Incubations were conducted for 60 minutes at 30° C. (EP3) or 45 minutes at 23° C. (EP2 and EP4). Incubations were terminated by rapid filtration through a 96-well Unifilter GF/B (Packard) (prewetted in 10 mM MES, 0.01% BSA, pH 6.0 for EP2) at 4° C. using a Filtermate 196 96-well semi-automated cell harvester (Packard). The filters were washed with 3-4 mL of wash buffer (20 mM HEPES pH 7.4 for EP3, 10 mM MES, 0.01% BSA, pH 6.0 for EP2 and EP4), dried for at least 1 hour at room temperature, and the residual radioactivity bound to the individual filters determined by scintillation counting with addition of 37.5 uL of Microscint 20 (Packard) using a Packard TopCount Microplate Scintillation Counter. Statistics of binding were determined using Prism v 3.0 software (GraphPad). Compounds of Formula I showed activity using the above assays.

Example 7

Bone Mass Density Assay

The compounds of this invention may be evaluated for their effect on bone mass in ovariectomized rats.

Adult Sprague-Dawley or Wistar Hanover female rats are either sham operated or ovariectomized by Charles River. On receipt, rats are housed in pairs in an environmentally controlled room and acclimatized for at least one week. Animals are pair fed while were housed on site.

Test compound are administered subcutaneously once a day started from 20 days post surgery for 5 weeks in 10% EtOH/saline or 20 mM phosphate buffer.

Before the treatment and at the end of the treatment, rats are scanned using High Resolution Software Package on a Hologic QDR-4500 Bone Densitometer to measure the bone mineral density (BMD). Scans are then analyzed using regions of interest, as designated below: whole femur, proximal femur, femur diaphysis, distal femur, distal femur metaphysis, proximal tibia, proximal tibia metaphysis, L2-L4 vertebrae, L5 vertebrae.

For a verification of the effect of ovariectomy on bone mass, the sham and OVX of like vehicle groups are compared using a students t-test. The OVX groups are compared by one way analysis of variance (ANOA), followed by Fisher's LSD to compare each treatment group to vehicle when the overall effect was statistically significant. The data could be ranked prior to the above analysis and corresponding non-parametric analysis is performed (Wilcoxon rank-sum test or Kruskal-Wallis).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the Formula I

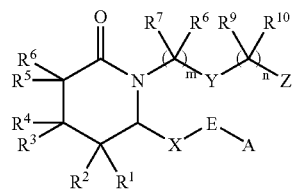

wherein:
m is from 1 to 4;
n is from 0 to 4;
A is:
cyclopropylethyl; 4'-chloro-2'-methyl-biphenyl; 4-hydroxy-3-methyl-benzyl; 3-(methoxy-methyl)-phenyl; 4-hydroxy-3-isopropyl-phenyl; 1-phenyl-cyclopropyl; 4-hydroxy-2'-methyl-biphenyl; cyclobutylethyl; 3-(3-fluorophenoxy)-phenyl; 2,5-dimethylphenyl; phenoxyymethyl; 3'-chloro-biphenyl; or 3-trifluoromethyl-benzyl;
E is —CHOH—;
X is —(CH$_2$)$_2$— or —CH=CH—;
Y is —CH$_2$—, —CH=CH—, —O—, —S(O)$_p$— where p is from 0 to 2, or —NR$^a$— where R$^a$ is hydrogen or alkyl;
Z is —COOR$^b$ where R$^b$ is hydrogen or alkyl; and
R$^1$, R$^2$, R$^3$, R$^4$, R$^5$, R$^6$, R$^7$, R$^8$, R$^9$ and R$^{10}$ each independently are hydrogen or alkyl;
or a pharmaceutically acceptable salt thereof.

2. The compound of claim 1, wherein Y is —CH$_2$—.
3. The compound of claim 1, wherein Y is —S(O)$_p$— and p is 0.
4. The compound of claim 2, wherein X is —CH=CH—.
5. The compound of claim 2, wherein X is —(CH$_2$)$_2$—.
6. The compound of claim 4, wherein A is 3-(methoxymethyl)-phenyl, 4-hydroxy-3-isopropyl-phenyl, 3-(3-fluorophenoxy)-phenyl, or 2,5-dimethylphenyl.
7. The compound of claim 4, wherein A is 4-hydroxy-3-methyl-benzyl or 3-trifluoromethyl-benzyl.
8. The compound of claim 4, wherein A is 1-phenyl-cyclopropyl.
9. The compound of claim 4, wherein A is cyclopropylethyl or cyclobutylethyl.
10. The compound of claim 4, wherein A is phenoxymethyl.
11. The compound of claim 5, wherein A is 3-(methoxymethyl)-phenyl, 4-hydroxy-3-isopropyl-phenyl, 3-(3-fluorophenoxy)-phenyl, or 2,5-dimethylphenyl.
12. The compound of claim 5, wherein A is 4-hydroxy-3-methyl-benzyl or 3-trifluoromethyl-benzyl.
13. The compound of claim 5, wherein A is 1-phenyl-cyclopropyl.
14. The compound of claim 5, wherein A is cyclopropylethyl or cyclobutylethyl.
15. The compound of claim 5, wherein A is phenoxyymethyl.
16. The compound of claim 3, wherein X is —CH=CH—.
17. The compound of claim 3, wherein X is —(CH$_2$)$_2$—.
18. The compound of claim 16, wherein A is 3-(methoxymethyl)-phenyl, 4-hydroxy-3-isopropyl-phenyl, 3(3-fluorophenoxy)-phenyl, or 2,5-dimethylphenyl.
19. The compound of claim 16, wherein A is 4-hydroxy-3-methyl-benzyl or 3-trifluoromethyl-benzyl.
20. The compound of claim 16, wherein A is 1-phenyl-cyclopropyl.
21. The compound of claim 16, wherein A is cyclopropylethyl or cyclobutylethyl.
22. The compound of claim 16, wherein A is phenoxyymethyl.
23. The compound of claim 17, wherein A is 3-(methoxymethyl)-phenyl, 4-hydroxy-3-isopropyl-phenyl, 3-(3-fluorophenoxy)-phenyl, or 2,5-dimethylphenyl.
24. The compound of claim 17, wherein A is 4-hydroxy-3-methyl-benzyl or 3-trifluoromethyl-benzyl.
25. The compound of claim 17, wherein A is 1-phenyl-cyclopropyl.
26. The compound of claim 17, wherein A is cyclopropylethyl or cyclobutylethyl.
27. The compound of claim 17, wherein A is phenoxyymethyl.
28. The compound of claim 1, wherein said compound is of the Formula II

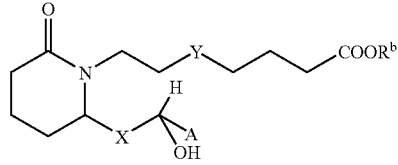

wherein Y is —CH$_2$— or —S—, and A, X and R$^b$ are as defined in claim 1.

29. The compound of claim 28, wherein said compound is of the Formula III:

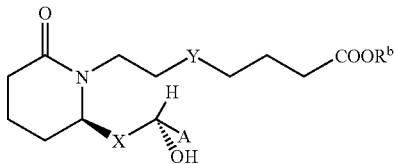

wherein A, X, Y and R$^b$ are as defined in claim 28.

30. A compound selected from;
4-{2-[(R)-2-((S)-(E)-5-Cyclopropyl-3-hydroxy-pent-1-enyl)-6oxo-piperidin-1-yl]-ethylsulfanyl}-butyric acid;
4-(2-{2R-[3R-(4'Chloro-2'methylbiphenyl-3-yl)-3-hydroxy-propyl]-6-oxo-piperidin-1-yl}-ethylsulfanyl) butyric acid;
7-{2R-[3S-Hydroxy-4-(4-hydroxy-3-methyl-phenyl)-but-1E-enyl]-6-oxo-piperidin-1-yl} heptanoic;
7-{2R-[3S-Hydroxy-4-(3-methoxymethyl-phenyl)-but-1E-enyl]-6-oxo-piperidin-1-yl} heptanoic acid;
7-{2R-[3S-Hydroxy-4-(4-hydroxy-3-isopropyl-phenyl)-but-1E-enyl]-6-oxo-piperidin1-yl} heptanoic acid;
4-(2-{2R-[3-Hydroxy-3-(1-phenylcyclopropyl)-prop-1E-enyl]-6-oxo-piperidin-1-yl}ethylsulfanyl) butyric acid;
4-(2-{2R-[3R-Hydroxy-3-(1-phenylcyclopropyl)-propyl]-6-oxo-piperidin-1-yl}ethylsulfanyl) butyric acid;

4-(2-{2R-[3S-Hydroxy-4-(3-methoxymethyl-phenyl)-but-1E-enyl]-6-oxo-piperidin-1-yl}ethylsulfanyl) butyric acid;

7-{2R-[3R-(4'-Hydroxy-2'-methylbiphenyl-3-yl)-3-hydroxy-propyl]-6-oxo-piperidin-1-yl} heptanoic acid;

7-{2R-[3-Hydroxy-3-(4'-hydroxy-2'methylbiphenyl-3-yl)-prop-1E-enyl]-6-oxo-piperidin-1-yl} heptanoic acid;

7-(2-{2R-[3R-(4'-Hydroxy-2'methylbiphenyl-3-yl)-3-oxo-propyl]-6-oxo-piperidin1-yl} heptanoic acid;

4-{2-[2R-(5-Cyclobutyl-3S-hydroxy-pent-1E-enyl)-6-oxo-piperidin-1-yl]ethylsulfanyl} butyric acid;

4-(2-{2R -[3R-(3'-fluorophenoxy-phenyl-3-yl)-3-hydroxy-propyl]-6-oxo-piperidin-1-yl}-ethylsulfanyl) 3-methyl-butyric acid;

4-{2-[2R-(3-Hydroxy-4,4-dimethyl-oct-1E-enyl)-6-oxo-piperidin-1-yl]-ethylsulfanyl} butyric acid;

7-{2R-[3-Hydroxy-3-(2,5-dimethylphenyl-3-yl)-prop-1E-enyl]-6-oxo-piperidin-1-yl} heptanoic acid;

7-[-2R-(3-Hydroxy-4-phenoxy-but-1E-enyl)-6-oxo-piperidin-1-yl]heptanoic acid;

7-{2R-[3-Hydroxy-3-(3'chloro-biphenyl-3-yl)-prop-1E-enyl]-6-oxo-piperidin-1-yl} heptanoic acid; and 7-{2R-[3R-(3'chloro-biphenyl3-yl)-3-hydroxy-propyl]-6-oxo-piperidin-1-yl} heptanoic acid.

31. A composition comprising a compound of claim 1 in admixture with at least one suitable carrier.

* * * * *